United States Patent
Barney et al.

(10) Patent No.: US 6,203,535 B1
(45) Date of Patent: Mar. 20, 2001

(54) METHOD OF MAKING AND USING A FLEXIBLE, MULTIPLE-COMPARTMENT DRUG CONTAINER

(75) Inventors: Ward W. Barney; Walter A. York; Douglas G. Harvey, all of Mission Viejo; Mark R. McLonis, Playa Del Rey; H. Theodore Young, Dana Point; Scott L. Pool, Laguna Hills; Giuseppe Sacca, Laguna Niguel; Sharilyn J. Sandberg, Rossmoor; Thomas R. Sakaguchi, Irvine; Steven L. Smith, Lake Forest; William V. Walter, Huntington Beach; Nicholas Chung-Hui Wu, Irvine; Noel Gharibian, Glendale, all of CA (US); Christopher D. Peara, Milwaukee, WI (US)

(73) Assignee: B. Braun Medical, Inc., Bethlehem, PA (US)

( * ) Notice: Subject to any disclaimer, the term of this patent is extended or adjusted under 35 U.S.C. 154(b) by 0 days.

(21) Appl. No.: 09/189,127

(22) Filed: Nov. 10, 1998

Related U.S. Application Data

(60) Division of application No. 08/837,927, filed on Apr. 11, 1997, now Pat. No. 5,944,709, which is a continuation-in-part of application No. 08/647,583, filed on May 13, 1996, now abandoned.

(51) Int. Cl.[7] .................................................. A61B 19/00
(52) U.S. Cl. ............................ 604/408; 604/410; 53/452
(58) Field of Search ................................... 604/408, 409, 604/411, 412, 415, 416; 53/410, 452, 455, 133.2, 425

(56) References Cited

U.S. PATENT DOCUMENTS

| | | | |
|---|---|---|---|
| 2,483,636 | 10/1949 | Hardesty | 128/227 |
| 2,663,298 | 12/1953 | Rose | 128/214 |
| 3,074,544 | 1/1963 | Bollmeier et al. | 206/47 |
| 3,257,072 | 6/1966 | Reynolds | 233/26 |
| 3,520,471 | 7/1970 | Faust | 229/56 |
| 3,545,671 | 12/1970 | Ross | 233/26 |

(List continued on next page.)

FOREIGN PATENT DOCUMENTS

| | | |
|---|---|---|
| 626563 | 4/1994 | (JP) . |
| 2675049 | 7/1997 | (JP) . |

OTHER PUBLICATIONS

Inoue, Fujio, A New Package For A Kit Product: A Multiple Chamber Plastic Bag Packaging Parenteral Powder Drug and Diluent, PDA Asian Symposium & Exhbit, Tokyo '94.
McGaw, Inc., Discussion Guide, (DUPLEX™ Focus Groups) Oct. 24, 1994, (3 pages).
Engineering Drawing No. S6272, entitled "Duplex Container, Oct. 1994".

Primary Examiner—John G. Weiss
Assistant Examiner—David J. Cho
(74) Attorney, Agent, or Firm—Christie, Parker & Hale, LLP

(57) ABSTRACT

A flexible container is provided for the storage and mixing together of diluents and medicaments. The container incorporates multiple compartments, separated by peelable seals, in which the diluents and medicaments are stored. The container is constructed of thermoplastic materials having high oxygen and moisture barrier properties which allows the container to be stored for extended periods of time without degrading the contents. The seals are ruptured by manipulation of the container to thereby mix the contents together for delivery through standard IV arrangement to a patient. The seals are constructed to provide a non-linear resistance characteristic to hydraulic pressure, which causes the seal to peel open completely along its length. The container is folded-over along the line of one of the seals and also includes a locking tab and retaining slot to secure the bag in a folded-over condition.

37 Claims, 17 Drawing Sheets

U.S. PATENT DOCUMENTS

| | | | |
|---|---|---|---|
| 3,554,256 | * 1/1971 | Anderson | 604/403 |
| 3,608,709 | 9/1971 | Pike | 206/47 A |
| 3,749,620 | 7/1973 | Montgomery | 156/73 |
| 3,756,389 | 9/1973 | Firth | 206/47 A |
| 3,794,490 | 2/1974 | Nerwin | 96/76 C |
| 3,809,224 | 5/1974 | Greenwood | 206/219 |
| 3,847,279 | 11/1974 | Montgomery | 206/219 |
| 3,882,259 | 5/1975 | Nohara et al. | 428/35 |
| 3,911,640 | 10/1975 | Rausing | 53/21 FC |
| 3,946,871 | 3/1976 | Sturm | 206/498 |
| 3,964,604 | 6/1976 | Prenntzell | 206/219 |
| 3,985,135 | 10/1976 | Carpenter et al. | 128/214 D |
| 4,010,786 | 3/1977 | Aguettant et al. | 150/8 |
| 4,183,434 | 1/1980 | Watt | 206/438 |
| 4,198,972 | 4/1980 | Herb | 128/214 |
| 4,223,512 | 9/1980 | Buchner | 53/425 |
| 4,224,367 | 9/1980 | Scholle | 428/76 |
| 4,236,652 | 12/1980 | Beguhn | 222/92 |
| 4,252,846 | 2/1981 | Romesberg et al. | 428/35 |
| 4,270,533 | 6/1981 | Andreas | 128/214 F |
| 4,284,672 | 8/1981 | Stillman | 428/35 |
| 4,313,904 | * 2/1982 | Larkin et al. | 264/515 |
| 4,375,145 | 3/1983 | Mosse et al. | 53/425 |
| 4,396,382 | 8/1983 | Goldhaber | 604/28 |
| 4,396,383 | 8/1983 | Hart | 604/56 |
| 4,401,214 | 8/1983 | Kleckers | 206/219 |
| 4,402,402 | 9/1983 | Pike | 206/219 |
| 4,409,775 | 10/1983 | Brody et al. | 53/167 |
| 4,410,321 | 10/1983 | Pearson et al. | 604/56 |
| 4,417,607 | 11/1983 | Scholle et al. | 141/1 |
| 4,432,763 | 2/1984 | Manschot et al. | 604/262 |
| 4,452,030 | 6/1984 | Inada | 53/426 |
| 4,458,811 | 7/1984 | Wilkinson | 206/219 |
| 4,465,488 | 8/1984 | Richmond et al. | 604/414 |
| 4,467,588 | 8/1984 | Carveth | 53/425 |
| 4,470,240 | * 9/1984 | Torterotot et al. | 53/455 |
| 4,484,920 | 11/1984 | Kaufman et al. | 604/416 |
| 4,496,046 | 1/1985 | Stone et al. | 206/219 |
| 4,507,114 | 3/1985 | Bohman et al. | 604/111 |
| 4,512,136 | * 4/1985 | Christine | 53/410 |
| 4,519,499 | 5/1985 | Stone et al. | 206/219 |
| 4,528,220 | 7/1985 | Hwo | 428/35 |
| 4,530,202 | 7/1985 | Powell et al. | 53/426 |
| 4,548,023 | 10/1985 | Danby et al. | 53/452 |
| 4,566,251 | 1/1986 | Spisak et al. | 53/167 |
| 4,588,554 | 5/1986 | Kaartinen et al. | 422/61 |
| 4,600,613 | 7/1986 | Yoshida | 428/35 |
| 4,602,910 | 7/1986 | Larkin | 604/87 |
| 4,608,043 | 8/1986 | Larkin | 604/87 |
| 4,610,684 | 9/1986 | Knox et al. | 604/416 |
| 4,614,267 | 9/1986 | Larkin | 206/221 |
| 4,619,650 | 10/1986 | Wisdom | 604/408 |
| 4,622,032 | 11/1986 | Katsura et al. | 604/122 |
| 4,629,080 | 12/1986 | Carveth | 215/11 |
| 4,693,052 | 9/1987 | Rebmann et al. | 53/167 |
| 4,702,963 | 10/1987 | Phillips et al. | 428/426 |
| 4,711,359 | 12/1987 | White et al. | 215/11.1 |
| 4,731,053 | 3/1988 | Hoffman | 604/89 |
| 4,742,667 | 5/1988 | Müller et al. | 53/167 |
| 4,770,295 | 9/1988 | Carveth et al. | 206/219 |
| 4,803,102 | 2/1989 | Raniere et al. | 428/35.2 |
| 4,805,767 | 2/1989 | Newman | 206/219 |
| 4,813,210 | 3/1989 | Masuda et al. | 53/425 |
| 4,837,084 | 6/1989 | Warren | 428/349 |
| 4,874,656 | 10/1989 | Rantanen | 428/216 |
| 4,910,085 | 3/1990 | Raniere et al. | 428/412 |
| 4,910,147 | 3/1990 | Bacehowski et al. | 435/296 |
| 4,961,495 | 10/1990 | Yoshida et al. | 206/209 |
| 4,965,108 | 10/1990 | Biel et al. | 428/35.7 |
| 4,965,109 | 10/1990 | Tucker et al. | 428/35.7 |
| 4,969,915 | 11/1990 | Hatanaka et al. | 53/425 |
| 4,979,347 | 12/1990 | Shibauchi et al. | 53/167 |
| 4,992,247 | 2/1991 | Foti | 422/304 |
| 4,994,056 | 2/1991 | Ikeda | 604/410 |
| 5,007,232 | 4/1991 | Caudill | 53/426 |
| 5,011,719 | 4/1991 | Gehrke et al. | 428/35.7 |
| 5,014,494 | 5/1991 | George | 53/425 |
| 5,069,017 | 12/1991 | Fabricius | 53/426 |
| 5,071,686 | 12/1991 | Genske et al. | 428/35.7 |
| 5,114,004 | 5/1992 | Isono et al. | 206/222 |
| 5,129,212 | 7/1992 | Duffey et al. | 53/426 |
| 5,131,760 | 7/1992 | Farmer | 383/210 |
| 5,176,634 | * 1/1993 | Smith et al. | 604/87 |
| 5,207,509 | 5/1993 | Herbert | 383/38 |
| 5,209,347 | 5/1993 | Fabisiewicz et al. | 206/219 |
| 5,240,525 | 8/1993 | Percec et al. | 156/60 |
| 5,257,985 | 11/1993 | Puhl | 604/410 |
| 5,259,844 | 11/1993 | Bilstad et al. | 604/403 |
| 5,267,646 | 12/1993 | Inoue et al. | 206/204 |
| 5,287,961 | 2/1994 | Herran | 206/219 |
| 5,306,269 | 4/1994 | Lewis et al. | 604/403 |
| 5,423,421 | 6/1995 | Inoue et al. | 206/219 |
| 5,425,447 | 6/1995 | Farina | 206/219 |
| 5,431,496 | 7/1995 | Balteau et al. | 383/38 |
| 5,458,244 | 10/1995 | Emori | 206/527 |
| 5,462,526 | * 10/1995 | Barney et al. | 604/85 |
| 5,484,633 | 1/1996 | Murschall et al. | 428/35.7 |
| 5,487,940 | 1/1996 | Bianchini et al. | 428/349 |
| 5,493,845 | * 2/1996 | Adolf et al. | 53/410 |
| 5,496,302 | * 3/1996 | Minshall et al. | 604/410 |
| 5,501,887 | 3/1996 | Tanaka et al. | 428/35.2 |
| 5,507,904 | * 4/1996 | Fisher et al. | 156/252 |
| 5,520,972 | * 5/1996 | Ezaki et al. | 428/35.2 |
| 5,854,347 | * 12/1998 | Laurin et al. | 525/66 |
| 5,976,300 | * 11/1999 | Buchanan et al. | 156/273.7 |
| 6,017,598 | 1/2000 | Kreischer et al. | 428/35.4 |

* cited by examiner

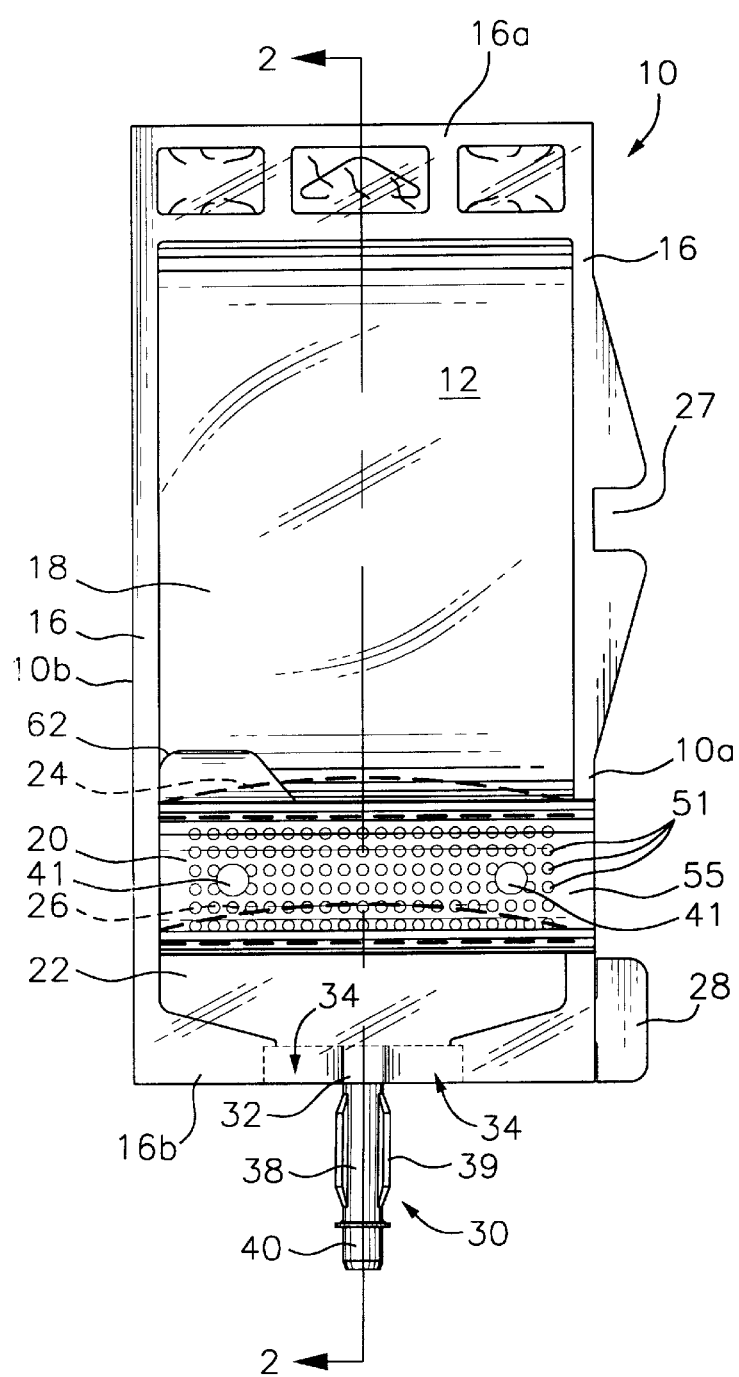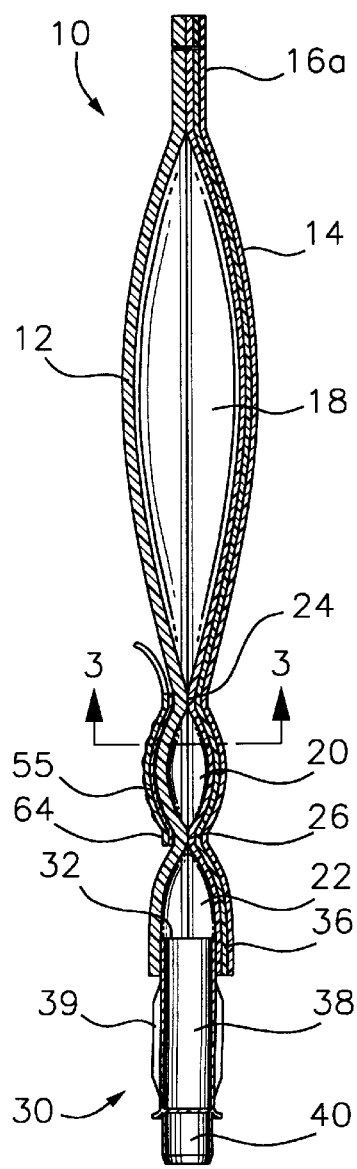

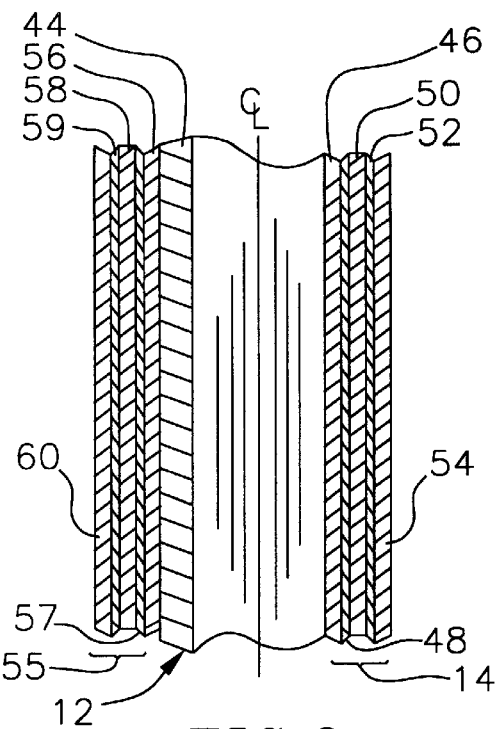
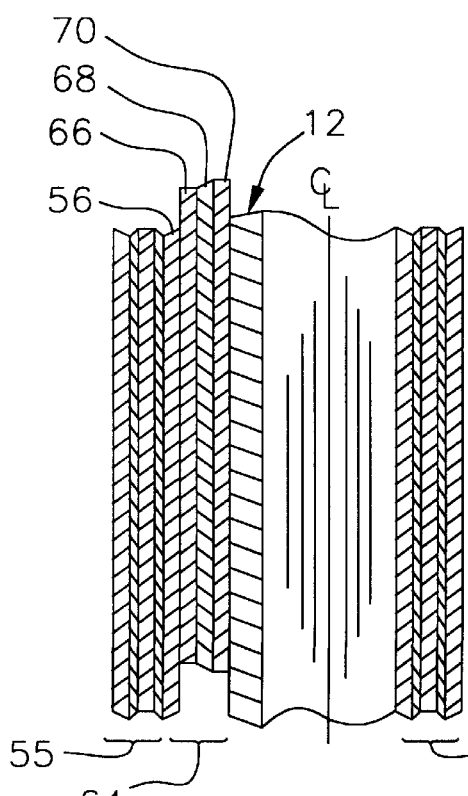
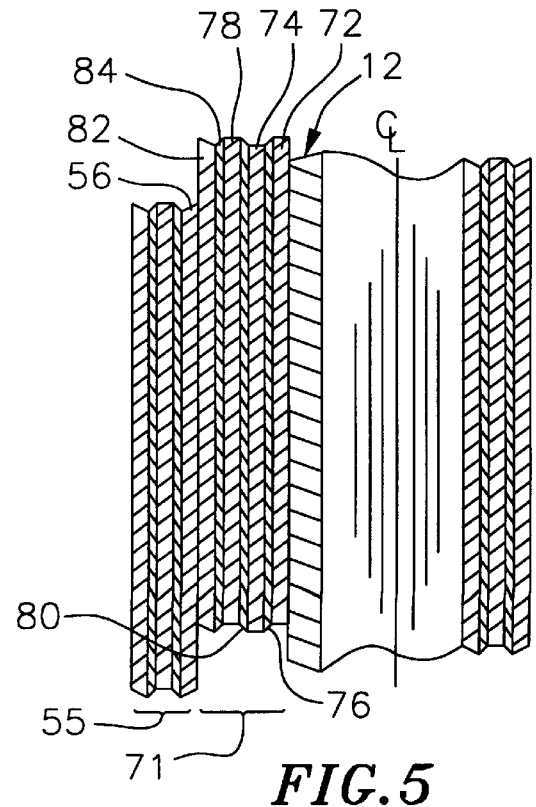
FIG.3
FIG.4
FIG.5

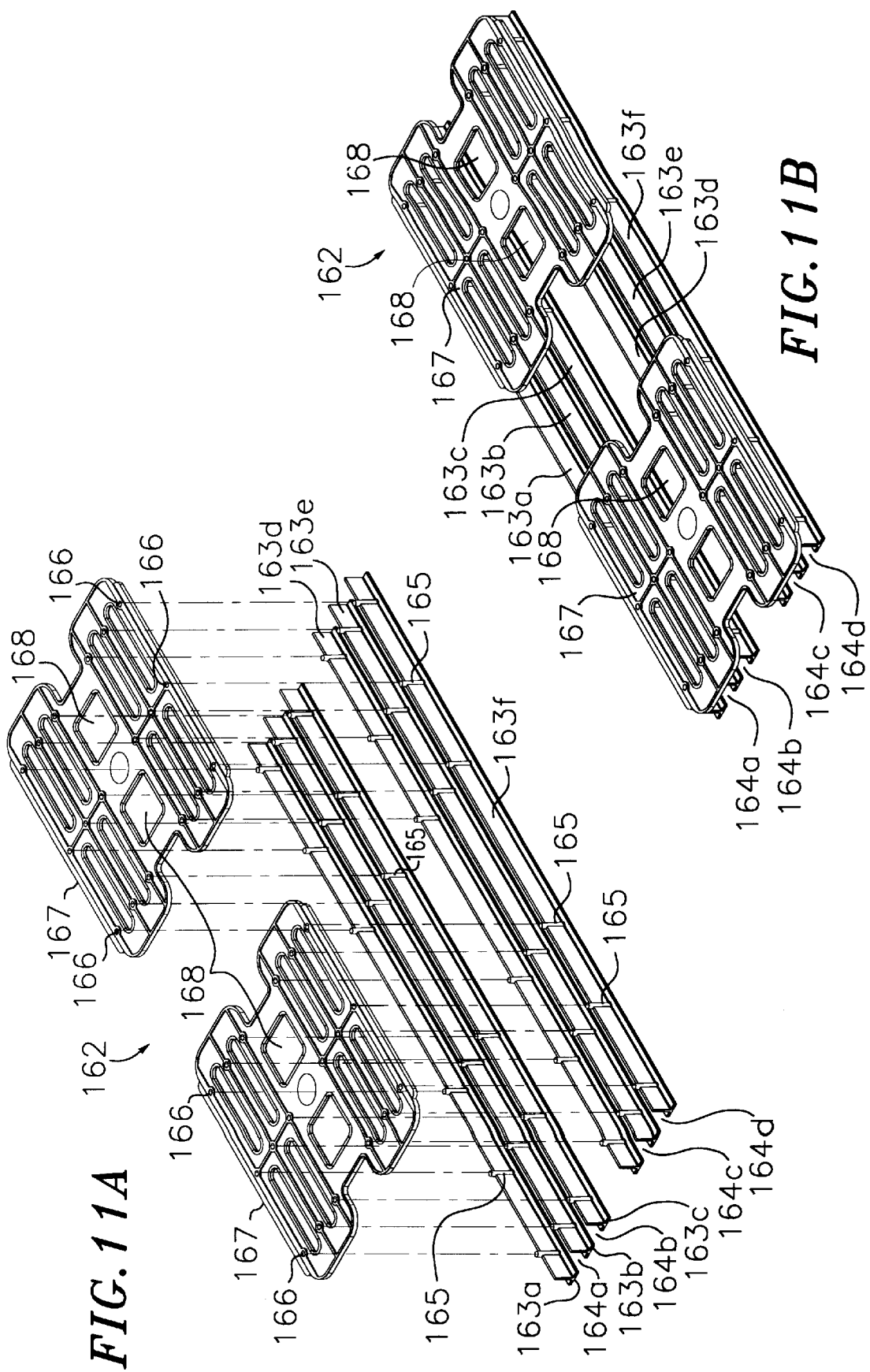

METHOD OF MAKING AND USING A FLEXIBLE, MULTIPLE-COMPARTMENT DRUG CONTAINER

CROSS-REFERENCE TO RELATED APPLICATION

This is division of Ser. No. 08/837,927 filed Apr. 11, 1997 now U.S. Pat. No. 5,944,709, which is a continuation-in-part of application Ser. No. 08/647,583 filed May 13, 1996, and now abandoned entitled "FLEXIBLE, MULTIPLE-COMPARTMENT DRUG CONTAINER AND METHOD OF MAKING AND USING SAME", the entire disclosure of which is incorporated herein by reference.

FIELD OF THE INVENTION

The present invention relates to flexible, sterile containers used for storing and mixing medicaments and diluent liquids in a sterile environment and for dispensing mixtures therefrom. More particularly, the container is manufactured from film webs using modular compartment-forming stations. The container is manufactured to include sacrificial ports by which the container is supported and transported through modular filling isolators.

BACKGROUND OF THE INVENTION

Various medicament (drug) solutions are commonly administered intravenously (via IV) from sterile containers to patients. Oftentimes, such solutions comprise a mixed combination of a liquid diluent, e.g., an aqueous dextrose or NaCl solution, and a medicament. Desirably, the medicament and diluent are stored separately in the container under aseptic conditions and are not mixed together until immediately prior to use so as to prevent degradation of the final product. Common packaging of the diluent and medicament is often further complicated by the character of the medicament which may be a powder sensitive to moisture contamination or a powder or liquid sensitive to degradation under light or oxygen exposure.

Accordingly, various medicaments, such as antibiotics, which become unstable with time in solution have been separately stored in moisture and gas-impermeable vials, containers, or the like prior to their use. Before being administered to a patient, medicaments stored in this fashion must be mixed, or diluted in, physiological solutions or diluents which are also preserved separately. While able to maintain medicament stability and effectiveness, separate component storage is cumbersome and involves the risk of bacteriological contamination during handling, mixing, and subsequent administration to a patient. Accordingly, medical containers have been developed which include a compartment for storing an unstable medicament and a compartment which contains a diluent liquid. Immediately prior to IV administration to a patient, the compartments are placed in communication with one another so that the contents can be mixed together aseptically.

Multiple compartment containers, which allow separate storage of liquid diluents and medicaments are known. Such containers are disclosed, for example, in U.S. Pat. No. 4,608,043 to Larkin and U.S. Pat. No. 5,176,634 to Smith, et al. U.S. Pat. Nos. 4,608,043 and 5,176,634 are expressly incorporated herein in their entirety by reference. The compartments of the containers disclosed in the foregoing patents are separated from one another by frangible heat seals. The seals are ruptured by manipulation of the container so that the contents of the compartments can be mixed together to thereby form a solution which is delivered to the patient through a standard IV arrangement.

Solution containers on the market today are generally manufactured of materials comprising PVC plastic. PVC material is generally quite murky in aspect, making it difficult to inspect the contents of a container manufactured of such material. Consequently, inspecting such containers for leaks and moisture contamination is quite difficult, as is verifying whether complete mixing of the medicament and diluent has taken place prior to administration to a patient. In addition, various hazardous chemicals are used in the manufacture of PVC material which must be disposed of in an environmentally safe manner. PVC containers must be carefully disposed of following their use, because PVC emits a toxic gas when incinerated and includes a toxic plasticizer that can leach into the surrounding environment if the container is buried in a land fill. This toxic plasticizer is also able to leach into IV solutions, making PVC containers unsuitable for use with several types of drugs.

The medicament compartment of such multi-compartment containers is desirably protected from moisture and atmospheric gasses as well as from exposure to UV and ambient radiation in order to avoid degradation of the medication contained therein. One known method of protecting the medicament compartment from, for example, moisture and oxygen contamination is disclosed in U.S. Pat. No. 5,267,646 to Inouye, et al., in which the medicament compartment is surrounded by a secondary compartment containing a desiccant and an oxygen absorber. Free oxygen and moisture vapor is allowed to penetrate the material of the secondary compartment, and is absorbed by the desiccant and oxygen scrubber before it is able to affect the material of the medicament compartment.

Although this method is able to provide some degree of protection for the medicament compartment against free oxygen and moisture, the method requires an additional layer of material (a secondary compartment) to be provided around the medicament, making it more difficult to inspect the contents of the medicament compartment prior to reconstitution. Moreover, no protection is provided against the effects of UV or ambient light degradation of the contents of the medicament compartment.

U.S. Pat. No. 5,176,634 to Smith et al. discloses a medical container having multiple compartments separated by peelable seals which may be ruptured by manually applying pressure to the exterior of the container. The container is formed of two sheets of flexible materials which are sealed together along their perimeter. Separate diluent and medicament compartments are formed in the container by frangible heat seals. The rear sheet is impermeable to water vapor and is constructed of a laminated material having an inner layer of polypropylene, a middle layer of aluminum foil and an outer layer of polyester film. Vapor impermeability of the rear sheet extends the shelf life of the product by reducing, by half, the permeation of diluent vapor from the container, and permeation of vapor from the atmosphere into the medicament compartment. Additional reduction in vapor permeability is provided for the medicament compartment by peelably affixing a third sheet of laminated material which is identical to the rear sheet, over the container front sheet in the region of the medicament compartment. This third sheet of laminated material is sized to cover the medicament compartment and, in combination with the rear sheet, provides a vapor impermeable enclosure.

However, once the vapor impermeable third sheet is peeled-away from the medicament compartment, the medicament compartment is no longer enclosed and therefore susceptible to vapor permeation from the atmosphere. In addition, moisture vapor is able to migrate from the diluent compartment into the medicament compartment through the material of the peelable seal which separates them. Because the vapor impermeable covering is routinely peeled-away from the medicament compartment during a hospital's incoming inspection procedure, long term storage of such containers is problematic. In cases where the medicament is a powder, highly susceptible to degradation by moisture, the shelf life of a container that has had its vapor impermeable covering removed is often no more than a few days.

In view of the foregoing, it can be seen that there is a need for an improvement over prior art containers in that there is a need for medical containers that are environmentally safe to manufacture and dispose of. Such containers should also be able to protect powdered and other sensitive medicaments from moisture and atmospheric gasses, while, at the same time, allowing easy visual access to the medicament compartment contents. Protection from UV and visible spectrum radiation is also desired.

In various prior art multiple compartment containers simple frangible, or peelable, seals are used to divide the medicament and diluent compartments to preclude the inadvertent delivery of any of the components prior to mixing. Such simple seals are formed across the container in its width direction, and have a uniform cross-sectional thickness and length throughout the entire seal. When the container is manipulated in order to rupture the seals, and, thereby, mix the medicament and diluent together prior to delivery, the mechanical pressure of the liquid diluent against a seal is relieved as soon as any portion of the seal ruptures and allows the diluent to enter the medicament compartment. Such a partial rupture of the linear seal often does not allow complete delivery of the fluid contents of the diluent compartment to the medicament. Significant quantities of diluent may remain in the diluent compartment, trapped in the corners defined by the sidewall of the compartment and the left and right ends of the seal. Such partial rupture also may result in incomplete mixing of medicaments with diluents and incomplete delivery of the mixed product to the patient.

It is therefore desirable to provide an IV container having multiple compartments for storage of diluents and medicaments in a single package having peelable seals dividing the compartments which are configured to be substantially completely ruptured along their entire length for complete combination and mixing of the contents, and to assure delivery of the total quantity of the final mixed product.

It is further desirable that the container arrangement preclude the inadvertent delivery of any of the components prior to mixing, but allow visual verification of the condition of the components following receipt of the container by a hospital's pharmaceutical services, but before storage and subsequent dispensing. The capability for enhanced protection of the contents of one or more of the compartments of the container against moisture, oxygen permeation or light degradation is also desirable.

SUMMARY OF THE INVENTION

The present invention provides a container having multiple compartments separated by peelable seals which may be ruptured by manually applying pressure to the exterior of the container. The container is formed of two sheets of flexible, laminated materials which are sealed together along their perimeters. Separate compartments in the container are formed by peelable heat seals. In a first embodiment of the invention, three compartments are formed in the container; the first compartment contains a liquid diluent, the second compartment contains a powdered medicament which may be mixed with a liquid diluent by separating the peelable seal dividing the two compartments, and the third compartment is an outlet compartment from which the mixed medication solution is dispensed.

In one aspect of the invention, the container is constructed of a flexible rear sheet and a flexible front sheet sealed to the rear sheet along a common peripheral edge. A first peelable seal extends between two sides of the common peripheral edge and separably joins the front and rear sheets to form a compartment containing a diluent. A second peelable seal extends between the two sides of the common peripheral edge and separably joins the front and rear sheets to form thereby an outlet compartment and a compartment containing a medicament which is intermediate the outlet compartment and the diluent compartment. A clear, high-barrier laminate film is sized to cover the medicament compartment and is sealed to the front sheet. An opaque high-barrier protective film is sized to extend over the clear high-barrier laminate film and the medicament compartment and is separably sealed to the clear high-barrier laminate film. The clear high-barrier film and the opaque high-barrier film, in combination, form a high-barrier protective covering over the medicament compartment.

In one embodiment, the opaque, high-barrier protective film includes an ethylenevinylacetate polymer layer on its inwardly facing surface; a polyester polymer layer, having a higher melting temperature than the ethylenevinylacetate polymer layer, on its outwardly facing surface; and an opaque high-barrier aluminum foil layer intermediate the ethylenevinylacetate and polyester layers. The opaque, high-barrier protective covering is peelably affixed over the medicament compartment for easy removal and subsequent inspection of the medicament compartment contents.

In another aspect of the present invention, the clear high-barrier laminate film comprises clear, transparent moisture and oxygen barrier laminate films provided intermediate the opaque, aluminum foil-containing protective film on the front sheet of the container, in the region of the medicament compartment. Specifically, the clear high-barrier laminate film comprises a polypropylene inner layer adjacent the container front sheet; an outer layer of polyester; and either a clear, transparent high-moisture barrier, a clear, transparent high-oxygen barrier, or both, disposed between the inner and outer layers.

In yet another aspect of the present invention, the peelable seals are constructed to present a curvalinear resistance characteristic to the hydraulic pressure on the seal caused by manipulating the container. The curvalinear resistance characteristic is stronger in the center of the peelable seal and decreases towards either side. Separating the seal is accomplished by manipulating the container to create pressure on the diluent in the first compartment which then hydraulically separates the seal substantially completely along its length between the compartments allowing the diluent and medicament to be mixed. A third compartment, adjacent the second compartment and opposite from the diluent compartment, contains an outlet port for dispensing the mixed fluid. A peelable seal between the second and third compartments prevents administration of the contents before mixing of the contents of the first two compartments. After mixing, additional manipulation of the container to exert pressure on the contents ruptures the second seal substantially completely along its length allowing the medicated fluid to be dispensed through the port.

In an additional embodiment of the invention, an additional, sacrificial moisture vapor barrier compartment is constructed intermediate the diluent and medicament compartments, by forming an additional peelable heat seal in advance of the peelable seal separating the diluent from the medicament compartment. In addition, the sacrificial moisture vapor barrier compartment provides additional protection for the medicament compartment against inadvertent rupturing of the medicament compartment seal.

In yet a farther aspect of the present invention, the medicament compartment is protected from premature exposure to liquid diluent by folding the container over in the region of the peelable seal formed between the medicament and diluent compartments. Folding the container over pinches the container material together in a region in advance of the first peelable seal, thus reinforcing the seal against hydraulic pressure caused by inadvertent manipulation of the container. Once the container is folded, means are provided to maintain the container in a folded-over condition. In one embodiment, a tab is inserted into a retaining slot, where both the tab and the retaining slot are integrally formed, along with the container, from the container materials. The container may, thus be repeatedly unfolded for periodic inspection of the container contents, and refolded for storage.

In another aspect of the present invention, the opaque high-barrier protective film is peelably affixed over the clear high-barrier laminate film to allow easy removal and inspection of the medicament compartment. Only a portion of the surface of the clear high-barrier laminate film is contacted by the opaque high-barrier protective film, the strength of attachment being directly proportional to the area of surface contact. The opaque high-barrier protective film is affixed over the clear high-barrier laminate film by a patterned heat seal head which defines a regular array of generally circular non-contact areas. The strength of the peelable seal thus formed is easily adjustable by varying the number of non-contact areas.

In yet a further aspect of the present invention, a method for forming a flexible container for combined storage and administration of medicaments and diluents for IV solutions comprises the steps of sealing a flexible transparent front sheet to a flexible, vapor impermeable rear sheet, along a common peripheral edge; heating the front and rear sheets in a first localized area to fuse together the heated portions of the adjoining surfaces, thereby forming a first peelable seal extending between two sides of the common peripheral edge; and heating the front and rear sheets in a second localized area to fuse together the heated portions of the adjoining surfaces, thereby forming a second peelable seal. The first peelable seal separably joins the front and rear sheets to thereby form a first compartment containing a diluent. The second peelable seal separably joins the front and rear sheets to thereby form an outlet compartment and a compartment for containing a medicament which is between the outlet compartment and the diluent compartment. First and second sacrificial ports are interposed between the front and rear sheets and are placed in communication with the diluent and medicament compartments, respectively. The diluent compartment is aseptically filled with a diluent solution through its respective sacrificial port and the seal along the container's periphery, in the region of the port, is completed. Likewise, the medicament compartment is aseptically filled with a medicament through its respective sacrificial port and that port is sealed-off along the container's periphery, following which the sacrificial ports are removed from the container. Container formation and filling is accomplished without the container's being subject to a sterilization step after the first compartment filling step.

Specifically, the diluent and medicament compartments are aseptically filled with pre-sterilized diluent and pre-sterilized medicament in a sterile environment. In one embodiment, the sterile environment is provided in an isolator within which the ambient atmosphere is maintained in a sterile condition.

In an additional embodiment of the invention, unfilled containers are placed in a transport carrier which is then sealed against environmental contamination. The transport carrier, and the containers within, are subject to E-beam sterilization. The transport carrier, and containers within, are introduced into the isolator through a UV decontamination tunnel, which ensures maintenance of a sterile environment inside the isolator.

BRIEF DESCRIPTION OF THE DRAWINGS

These and other features, aspects and advantages of the present invention will be more fully understood when considered with regard to the following detailed description, appended claims and accompanying drawings wherein:

FIG. 1 is a semi-schematic front view of one exemplary embodiment of the container provided in accordance with practice of the present invention showing the arrangement of the compartments and intervening curvalinear seals including an outlet port and fold-over locking tabs;

FIG. 2 is a semi-schematic side cross-sectional view taken along line 2—2 of FIG. 1, depicting the flexible sheets forming the container, the thickness of the layers in the sheets is exaggerated for clarity;

FIG. 3 is a semi-schematic fragmentary cross-sectional view taken along the line 3—3 of FIG. 2, showing the configuration of the flexible sheets of a first embodiment of the container of the present invention without the optional, transparent high-barrier intermediate layer;

FIG. 4 is a semi-schematic fragmentary cross-sectional view of the configuration of the flexible sheets of a first embodiment of the invention depicting an optional, transparent, high-barrier intermediate film;

FIG. 5 is a semi-schematic fragmentary cross-sectional view showing the laminate configuration of the flexible sheets of a second embodiment of the container of the present invention depicting a second embodiment of an optional, transparent, high barrier intermediate film;

FIG. 11a is a semi-schematic perspective view of the components of the rail cartridge of FIG. 10, depicting the rail cartridge in exploded form and ready for assembly;

FIG. 11b is a semi-schematic perspective view of the completely assembled rail cartridge of FIG. 11a;

DETAILED DESCRIPTION

Figure 6:
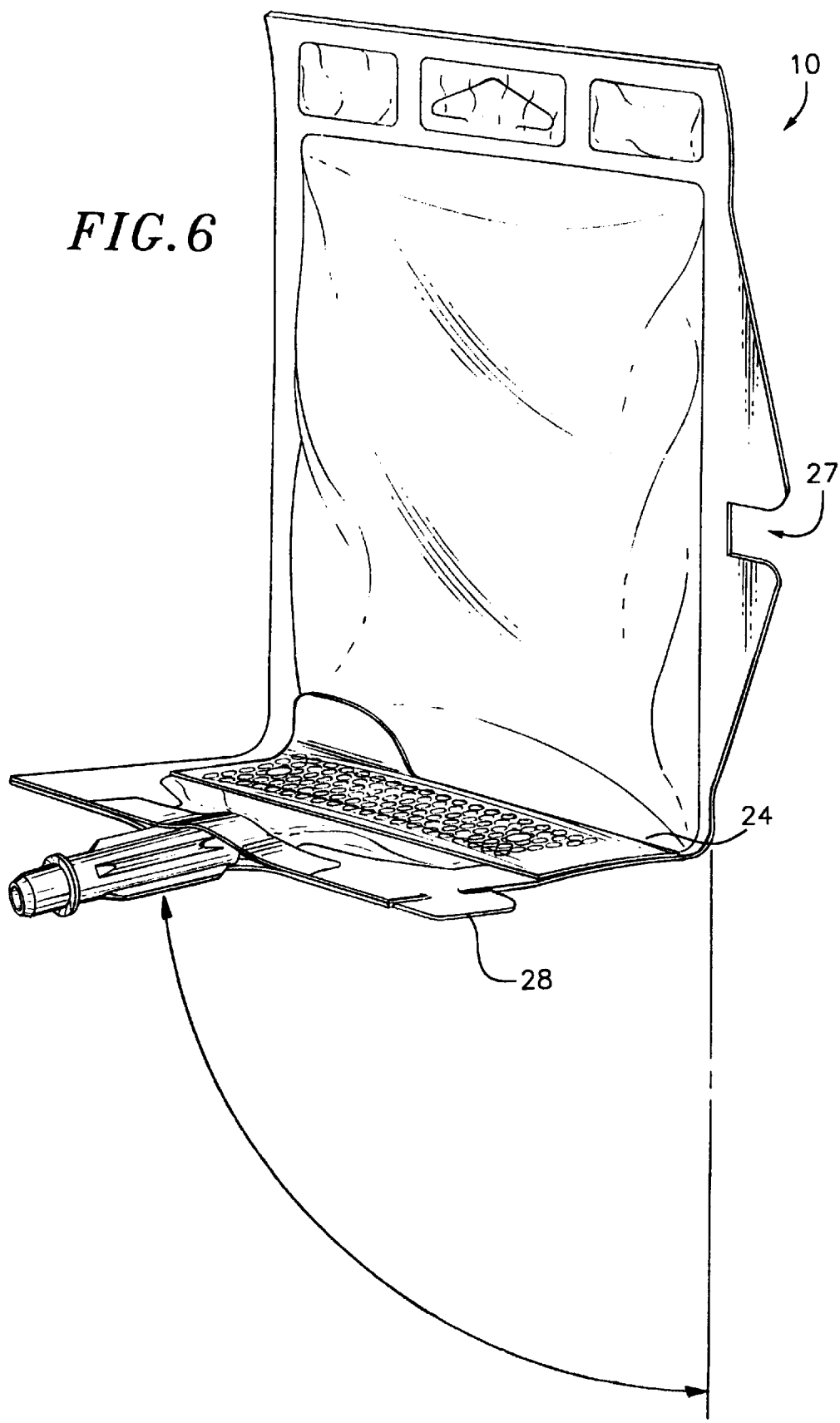
FIG. 6 is a semi-schematic front view of the embodiment of the container of FIG. 1, showing, the container being folded-over for storage.

Referring to FIGS. 1 and 2, there are shown schematic front and cross-sectional side views, respectively, of a preferred embodiment of a flexible, sterile container 10 provided in accordance with practice of principles of the present invention. Although the container 10 can be viewed in any orientation, for purposes of explanation herein, the position of the compartments of the container relative to one another are described as positioned in FIGS. 1 and 2. The container 10 is formed from a front sheet 12 and a back or rear sheet 14 (shown only in FIG. 2). The front and back sheets may be constructed of a single layer of flexible material or multi-layer laminates of flexible material to be described in greater detail below. The sheets forming the container can be provided separately and then sealed together at their common peripheral edge, forming an edge seal 16 which extends around the entire periphery of the container. Such peripheral seals may vary in configuration and width. A patterned seal, such as that depicted on the top seal portion 16a and the bottom seal portion 16b in FIG. 1 may be used to provide grasping areas for the user to handle the container and for the attachment of the container to, for example, an IV support stand. Alternatively, the front and rear sheets can be formed from a single film sheet which is subsequently folded-over and sealed by means of a heat seal which extends around the peripheral portion of the container. The sealed-together sheets are referred to herein as the "shell" or "body" of the container.

In the present embodiment, the container 10 is partitioned into three separate compartments; an upper compartment 18, an intermediate compartment 20 and a lower compartment 22, each of which is sterile. The upper and intermediate compartments 18 and 20 are separated from one another by a first peelable seal 24, and the intermediate and lower compartments 20 and 22 are separated from one another by a second peelable seal 26. The peelable seals 24 and 26 extend between the two sides of the container, i.e., between the right side 10a and the left side 10b joining the front and rear sheets. A "peelable" seal as the term is used herein is a seal which is sufficiently durable to allow normal handling of the container yet which will peel, allowing separation of the front sheet from the back sheet in the region of the seal, under hydraulic pressure applied by manipulating the container, thereby allowing mixing and dispensing of the container contents. A peelable seal is formed by a partial melting together of the polymer present in the adjacent layers of the front and back sheets. The seal is obtained by a heat sealing process which is performed with varying times, temperatures, and pressures to be described in greater detail below. Conversely, the peripheral edge seal 16 is significantly stronger than the "peelable" seals and will not be ruptured by pressures generated to separate the peelable seals. Configuration of the peelable seals with a non-linear resistance to the hydraulic opening pressure of a manipulated container, as contrasted to a conventionally formed straight-line seal, promotes substantially complete peeling of the entire seal during use of the container as will be described in greater detail subsequently.

In a typical application for the container 10 of the present invention, the upper compartment 18 is filled with a liquid diluent and the intermediate compartment 20 is filled with a medicament, typically provided in powder form. The lower compartment 22 functions as a security interface for an outlet port 30 and remains empty until the container is used. The outlet port 30 extends downwardly from a conformal saddle 32 which, when viewed from above, is shaped like an ellipse with its focal ends flattened, and is disposed in about the center of the container's lower edge between the front sheet 12 and the rear sheet 14. The flattened focal ends of the saddle 32 form flanges 34, best seen in FIG. 1, which taper towards the flattened edges of the saddle 32. The flattened elliptical shape creates a smoothly curved surface to which the front and rear sheets are firmly attached by, for example, a permanent heat seal (termed herein the "outlet seal") 36 (shown in FIG. 2). The outlet port 30 comprises a body portion 38 and a nozzle 40 which is configured for attachment to a standard IV administration device. A cap (not shown) is provided to cover the nozzle and maintain its sterility. The cap is removed just prior to attachment of an IV set to the outlet port. Ribs 39 are provided in spaced-apart relationship about the body portion 38 of the outlet port 30 to give a surface that may be easily grasped when attaching an IV set to the container. In the illustrated embodiment, four ribs 39 are provided which extend longitudinally from the surface of the body portion 38 of the container 10. While four longitudinal ribs are depicted, one having skill in the art will recognize that various other types of surface articulation may be provided that will allow the port to be easily grasped, such as circumferential ribs, transverse ribs, knurling or crosshatching of the body portion surface, and the like.

The materials employed in the front and rear sheets of the container 10 are selected based on the material to be stored therein. Preferably, at least one of the sheets is transparent to allow the contents of the container to be visually inspected and to allow the level of the solution in the container to be seen during dispensing. Suitable materials for fabrication of the transparent sheet are typically single-layer and multi-layer laminated, polymer films.

In particular, whether constructed of a single layer or a multi-layer laminated polymer film, the materials comprising the front 12 and rear 14 sheets of the container 10 are chosen for their clarity and transparency. Conventional polyvinylchloride (PVC) container materials are generally quite murky in appearance, making it difficult to adequately view the interior of the container and determine the levels of any fluids contained therein or the presence of particulate matter. This is a particularly dangerous situation when administering medication intravenously. It is imperative that a nurse or clinical worker be able to tell, at a glance, that the fluid of any such medication being administered from a medical container is free from particulate matter.

The First Embodiment

In a first embodiment of the container of the present invention, which is depicted in fragmentary schematic cross-section in FIG. 3, the front sheet 12 is constructed of a transparent, single-layer, thermoplastic polymer film 44. In this embodiment the transparent film 44 comprises a blend of about 80% by weight polypropylene-polyethylene copolymer available from Fina Oil and Chemical Company, of Deerpark, Tex., having a commercial designation of Z9450, and about 20% by weight styrene ethylene-butylene styrene thermal plastic elastomer, available from Shell Chemical Corporation under the trade name KRATON® and having a commercial designation G1652. Kraton® G1652 thermal plastic elastomer is a three block copolymer with polystyrene end blocks and a rubbery poly (ethylene-butylene) midblock. In practice, the film is made by mixing pellets of the co-polymer resin and KRATON® in crumb form in the 80%/20% by weight ratio, in a high shear mixer and melting and repelletizing the mixture. Subsequently, the transparent film 44 is formed from the blended pellets in a commercial extrusion apparatus. The transparent polymer film 44 comprising the front sheet 12 may be constructed with varying thicknesses, depending on the use to which the container is put, and the durability required for that application. Suitable thicknesses for the material comprising the front sheet 12 may range from about 3 to about 15 mils. In one preferred embodiment, the transparent polymer film 44 comprising the front sheet 12 has a thickness of 12 mils.

In addition to its clarity and transparency, the transparent polymer film 44 (which may be referred to alternatively as the "80:20 film") is particularly suitable for forming both "peelable" seals and permanent edge seals along the periphery of the container 10. As will be described in greater detail below, the 80:20 film, in accordance with the invention, is able to accommodate both lower-temperature peelable seal, and higher-temperature permanent seal, formation processes without affecting the material's integrity or its ability to provide an effective peelable seal.

For certain combinations of diluents and medicaments, the rear sheet 14 can have the same single layer composition and configuration as the front sheet 12. Alternatively, multi-layer films which include layers which are impermeable to moisture and light, for example, may be preferred for the rear sheet to extend the shelf life of a filled container. In the embodiment of the container depicted in FIG. 3, a three-layer, laminate rear sheet 14 is employed which is impermeable to water vapor and to light in order to preserve the effectiveness and activity of the binary components (the unmixed medicament and diluent), thus increasing the shelf life of the filled container.

In the exemplary embodiment, the rear sheet 14 includes an inner, seal layer 46 on its inwardly facing surface, constructed of an 80%/20% wt/wt blend of polypropylene-polyethylene copolymer and styrene ethylene-butylene styrene thermal plastic elastomer having a thickness of about three to six mils (the 80:20 film). In one preferred embodiment, the inner seal 80:20 film layer 46 is a six mil thick composition, which is bonded by means of a suitable transparent adhesive 48 to an approximately 0.7 mil to 1.3 mil (preferably 1.0 mils) high-barrier aluminum foil layer 50. An outer, high melting temperature layer 54 is provided on the rear sheet's outwardly facing surface, and is bonded to the high-barrier aluminum foil layer 50 by means of a suitable transparent adhesive 52. In the embodiment of FIG. 3, the adhesive layers 48 and 52 comprise a modified aliphatic polyester polyurethane adhesive, available from Liofol Co. of Cary, N.C., under the commercial designation TYCEL 7909. The aluminum foil layer 50 is suitably constructed of a commercially available 1 mil. aluminum foil, such as Alcan 1145, available from the Alcan Rolled Products Company of Louisville, Ky.

Because the heat sealing process used to form the peripheral edge seals and the transverse peelable seals is capable of damaging the high-barrier aluminum foil layer, were that layer to remain exposed, the outer high temperature layer 54 is constructed of a relatively high-melting polymer and functions as a protective layer to prevent contact between the foil layer and the hot patterns of a heat seal apparatus. Further, the high-temperature layer 54 serves as a heat seal release (also termed mold release) because it does not melt and stick to the heat seal platens at the temperatures used to form the seals.

The outer high-temperature layer 54 is preferably a polyethylene terephthalate (designated herein as PET or polyester) available from Rhone-Poulanc under the commercial designation TERPHANE 10.21, having a thickness of in the range of about 0.4 to about 0.6 mils. In one preferred embodiment, the thickness dimensions of the multi-layer laminate film 14 are 0.48 mils for the outer, higher-temperature polyester layer 54, 1.0 mils for the high-barrier aluminum foil layer 50, and 6.0 mils for the 80:20 film inner seal layer 46.

It has been found that preferable material choices for the front and rear sheets, which result in optimum performance of the peelable seals, incorporate an interfacing seal layer on both sheets comprising the 80:20 film. However, the interfacing seal layers of the front and rear sheets may, alternatively, comprise polypropylene-polyethylene co-polymer and styrene ethylene-butylene styrene thermal plastic elastomer blends having differing relative percentages. The relative percentages used will depend on the characteristics of the various seals contemplated for use in connection with a particular medical container, and the temperature and pressure parameters of the sealing process. Other types of flexible films, which may be useful in the construction of the front and rear sheets of the shell of the container 10 of the present invention, as well as the interfacing seal layers on both sheets, are disclosed in U.S. Pat. Nos. 4,803,102, 4,910,085, 5,176,634, and 5,462,526, all of the disclosures of which are expressly incorporated herein by reference.

In certain applications, particularly where the medicament is in powder form, additional protection for the second or intermediate compartment 20 of the container 10 is preferred. Such additional protection is provided to preclude moisture, oxygen and/or light transmission through the film comprising the front of the intermediate compartment to protect the medicament powder from degradation. Such additional protection allows the container 10 to be stored, for substantial periods of time, without losing medicinal efficacy.

Referring in particular to FIGS. 2 and 3, an opaque, high-barrier protective film 55 is employed, in the illustrated embodiment, to cover the intermediate compartment 20. The film 55 interposes a barrier to moisture vapor and free oxygen permeation into the medicament compartment. In the exemplary embodiment, the high-barrier protective film 55 comprises a multi-layer laminate structure including a high-barrier aluminum foil layer. The use of an opaque aluminum foil laminate further helps prevent the medicament contained in the intermediate compartment 20 from being degraded due to exposure to visible light and UV radiation. Thus, in the present embodiment, the opaque aluminum foil comprising both the protective film 55 and the rear sheet 14 prevents penetration of UV and visible spectrum light into the intermediate compartment 20 of the container.

The high-barrier protective film 55 is a multi-layer laminate, constructed of an inner seal layer 56, on its inwardly facing surface. In an exemplary embodiment, the seal layer 56 is a soft co-extrusion coated resin comprising a modified ethylenevinylacetate polymer available from the Dupont Chemical Company under the commercial designation APPEEL 1181, provided in a thickness of from about 0.2 to about 0.4 mils. An aluminum foil layer 58, such as Alcan 1145, of from about 0.7 to about 1.3 mils, (preferably about 1.0 mils) thickness is bonded to the inner seal layer 56 by means of a suitable transparent adhesive 57. An outer, heat seal release layer 60 comprising a polyethylene terephthalate (PET) film, such as TERPHANE 10.21, approximately 0.48 mils in thickness, forms the outwardly facing surface of the high-barrier protective film 55 and is bonded over the aluminum foil layer 58 by means of a suitable transparent adhesive 59. The adhesive layers 57 and 59, of the present embodiment, comprise a modified aliphatic polyester polyurethane adhesive available from Liofol Co. under the commercial designation TYCEL 7909.

Because the inner seal layer 56 of the high-barrier protective film 55 is a co-extrusion coated resin, it is able to provide a peelable seal, over a broad temperature range, when applied to a number of different materials. Materials to which such a co-extrusion coated resin forms a peelable seal include acrylonitrile-butadiene-styrene (ABS), high density polyethylene (HDPE), high impact polystyrene (HIPS), polypropylene (PP), polystyrene (PS), polyvinylchloride (PVC), and the 80:20 film comprising the front sheet 12. The high-barrier protective film 55 may, thus, be removably (peelably) affixed to the outer surface of the front sheet 12, covering the intermediate compartment 20.

Preferably, the high-barrier protective film 55 is removable (peelable) from the container 10 prior to its use, to allow examination of the state of the medicament powder in the interior of the intermediate compartment 20. In the exemplary embodiment, best seen in connection with FIG. 1, the protective film 55 includes an extending tab 62 which may be grasped in order to peel the protective film 55 away from the transparent front sheet 12. The contents of the intermediate compartment 20 are thereby exposed and can be visually inspected.

As can be understood by referring to FIG. 1, the high-barrier protective film 55 is not affixed to the container by a seal over its entire surface area; rather, the film 55 is only partially sealed to the underlying material. Those portions of the high-barrier protective film 55 which are not sealed define a regular array of generally circular raised dimples 51, which are the tactile residue of a heat seal bar into which a rectangular array of holes has been cut. When the heat seal bar is pressed over the surface of the high-barrier protective film 55, a heat seal is provided only on the surface contact regions of the heat seal bar and not in the regions where the bar material has been removed (the holes). Since pressure is also applied along with heat, during the process, the high-barrier protective film 55 takes an impression from the heat seal head, thus giving rise to the textured, raised dimpled surface.

The dimples 51 allow the high-barrier protective film 55 to be adequately sealed over the underlying material of the medical container but, at the same time, provide for easy removal of the film 55 without the application of undue force. Were the entire protective layer 55 to be heat sealed onto the surface of the container, a larger than desired amount of force would be required to completely peel it away. By reducing the surface area of the seal, a lesser force (proportional to the seal area) is required to remove the peelable aluminum strip. It is apparent from the foregoing description, that the amount of force required to remove the peelable aluminum strip is inversely proportional to the number of dimples (51 of FIG. 1) formed in the film 55. Depending on the use to which the medical container is put, a more or less easily removable high-barrier protective layer may be easily constructed by merely increasing or decreasing the number of dimples 51 formed in the layer during the heat seal process.

In practical use, the filled container is received by a hospital's pharmacy services, and is then stored for a period of time against need. Typically, prior to dispensing, the pharmacist removes the high-barrier foil layer 55 from the surface 4 the container, thus exposing the medicament compartment 20 in order that the integrity of the contents may be visually verified. If the container is not put into use at that time, it is returned to the pharmacy and dispensed again, at the next request. The removal of the peelable high-barrier film 55 from the medicament compartment 20 leaves the contents of the medicament compartment susceptible to degradation by moisture, light and permeable oxygen. It is desirable that the filled containers, of the present invention, are able to be stored in pharmacy services for periods of time up to 30 days, prior to use, without the medicament being severely degraded by exposure to moisture and free oxygen after the high-barrier protective film over the medicament compartment has been removed.

Accordingly, as is shown in FIG. 4, in one embodiment of the present invention, a transparent high-barrier intermediate laminate film 64 is optionally interposed between the high-barrier aluminum foil-containing protective film 55 and the medicament compartment 20. The transparent high-barrier intermediate film 64 covers and protects the contents of the medicament compartment 20, after the peelable protective film 55 is removed from the container, from at least moisture vapor and free oxygen permeation for a substantial period which, depending on the activity of the contents of the medicament compartment, may be as long as 30 days. In other words, the opaque, high-barrier protective film 55 in combination with the transparent, high-barrier intermediate film 64 forms a high-barrier protective covering over the medicament compartment.

Polymers are classified by the degree to which they restrict passage of penetrant gasses, e.g., oxygen or moisture vapor. The categories range from high-barrier (low permeability) to low-barrier (high permeability). The category in which a polymer is classified may vary according to the penetrant gas. As used herein, the term "high barrier", when it refers to moisture vapor permeability, means a film with a permeability of less than about 1.5 g/mil/m$^2$/24 hr/atm, at 38° C., 100% R.H. As used herein, the term "high barrier" when it refers to oxygen permeability means a film with a permeability of less than about 50 cc/mil/m$^2$/24 hr/atm, at 25° C., 100% R.H.

In one exemplary embodiment, the transparent high-barrier intermediate film 64 comprises a three-layer high-barrier laminate structure which is significantly resistant to free oxygen and water vapor permeability so as to protect the contents of the medicament compartment and increase shelf life of the binary container. In one embodiment, the intermediate film 64 includes an outer layer 66 of silica deposited polyethylene terephthalate (also termed SiO$_x$ coated polyester or SiO$_x$ coated PET), available from Mitsubishi Kasei under the commercial designation TECH BARRIER™ H, in contact with the sealant layer 56 of the high-barrier protective film 55. The outer layer 66 is bonded to an intermediate layer 68 comprising a silica deposited (SiO$_x$ coated) polyvinyl alcohol (PVA) film available from Mitsubishi Kasei under the commercial designation TECH BARRIER™ S. On its inwardly facing surface, the transparent, high-barrier intermediate film 64 includes an inner seal layer 70 comprising a polypropylene-polyethylene co-polymer, which may be blended with styrene ethylene-butylene styrene thermal plastic elastomer in various ratios. However, a 100% polypropylene-polyethylene co-polymer layer is preferred. The individual layers of the intermediate laminate film 64 are adhesively bonded to one another. For clarity, however, these adhesive layers are not shown but comprise a modified aliphatic polyester polyurethane laminate available from Liofol Co. under the commercial designation TYCEL 7909. The inner seal layer 70 is securely affixed to the outer surface of the container front sheet 12 by an appropriate permanent heat or ultrasonic seal, an adhesive pressure seal, or the like. The transparent, high-barrier intermediate laminate film 64 is sized, horizontally and vertically, to cover the entire surface area of the medicament compartment and also extends to cover the peelable and permanent seals formed adjacent the medicament compartment.

As is the case with the flexible, plastic materials which comprise the front sheet 12 of the container body, the three-layer laminate structure of the intermediate layer 64 is substantially transparent to allow inspection of the contents of the medicament compartment 20. Thus, unlike polyvinylchloride (PVC), and other similar materials, which are fairly hazy (translucent), the intermediate layer 64 of the present invention is substantially clear and transparent, allowing the contents of the medicament compartment to be easily inspected, while imparting considerable protection against moisture and free oxygen degradation.

In particular, the barrier properties of the transparent, high-barrier intermediate laminate film 64 are substantially greater than those of conventional films, such as low-density polyethylene (LDPE), medium-density polyethylene (MDPE), linear low-density polyethylene (LLDPE), ethylene-vinyl acetate copolymers (EVA), or blends of these polymers, in areas important to the function of the container, e.g., moisture and oxygen permeability. The oxygen permeability of the intermediate layer 64 is approximately 10 cc/mil/m$^2$-24 hr/atm. Conversely, the oxygen permeability of EVA copolymers, LDPE and MDPE, respectively, are approximately 2500 (EVA 5%), 8300 (LDPE), and 8500 (MDPE) cc/mil/m$^2$-24 hr/atm. The oxygen permeability of LLDPE is approximately the same or slightly higher than LDPE. Thus, the oxygen permeability of the transparent, high-barrier intermediate layer 64 is orders of magnitude less than the oxygen permeability of polymers typically used to construct binary medical containers.

Because of the intermediate laminate film's barrier properties, the peelable aluminum foil-containing protective film 55 may be removed by a pharmacist in order to perform an inspection on the container's contents prior to dispensing, and the container may then be stored for an additional period of time without the danger of oxygen or moisture induced medicament degradation. Once the protective foil layer is removed, it is desirable that the container have a storage shelf life of about 30 days. After removal of the aluminum foil layer, the precise shelf life of a container which includes a clear high barrier laminate film 64 depends necessarily on the moisture sensitivity of the drug contained in the medicament compartment. Drugs with a relatively low moisture sensitivity are able to retain efficacy for periods substantially longer than 30 days by virtue of being protected by the clear high barrier laminate film 64. In addition, drugs with an extreme moisture sensitivity, i.e., those that would normally begin to loose effectiveness almost immediately upon removal of the aluminum foil layer, may be stored for periods up to two weeks without loosing effectiveness because of the moisture barrier properties of the clear high barrier film overlying the medicament compartment.

Although the intermediate barrier film 64 has been described in the exemplary embodiment as being affixed to the outer surface of the medicament compartment, it will be apparent to one skilled in the art that the intermediate layer may be sized to cover both the medicament and the diluent compartments if desired. The manner of attachment of the intermediate layer to the outer surface of the container may also be varied without departing from the scope of the invention. The intermediate layer 64 may be permanently secured to the outer surface of the container by a suitable adhesive, as well as by permanent heat or ultrasonic sealing. Alternatively, the intermediate film 64 may be removably provided on the surface of the container by adjusting the temperature and pressure characteristics of a heat seal, in order to make the seal peelable. In this case the film 64 could be peeled from the container 10 as was the case with film 55.

It should be noted that in the exemplary embodiment, the medicament is disclosed as being in the form of a dry powder. Such dry powders can be for example, antibiotic compositions or antiemetic compositions, with non-limiting examples of such being; cefazolin, cefuroxime, cefotaxime, cefoxitin, ampicillin, nafcillin, erythromycin, ceftriaxone, metoclopramide and ticar/clav. However, a liquid medicament may also be employed in this system. Such a condition may arise when a liquid medicament and a liquid diluent are not compatible for long periods of time and must be mixed just prior to being dispensed to a patient. Also, the medicament may be in the form of a colloid, crystalloid, liquid concentrate, emulsion, or the like. In addition, the medicament compartment need not be filled with a drug, per se. Other medical compositions, such as lyophilized blood fractions, blood factor 8, factor 9, prothrombin complex, and the like, are equally suitable. While a single medicament, and a single diluent compartment is disclosed in the container of the present invention, containers which have multiple compartments filled with different diluents and/or different medicaments, may be provided in accordance with the present invention.

The Second Embodiment

In a second exemplary embodiment of the present invention, which is depicted in schematic cross-section in FIG. 5, an alternative construction is provided for the transparent, high-barrier, intermediate laminate film (64 of FIG. 4), which covers the medicament compartment.

As was the case with the first embodiment, depicted in FIGS. 2, 3, and 4, the clear high-barrier intermediate laminate film 71 of FIG. 5, may be provided in combination with an opaque, high-barrier, aluminum foil-containing protective film (55 of FIGS. 2 and 3) disposed over the intermediate film 71 and, thus, also over the medicament compartment of the container. Accordingly, the clear, high-barrier intermediate film 71 in combination with an opaque, high-barrier protective film, comprises a high barrier protective covering disposed over the medicament compartment. As will be described in greater detail below, the high barrier protective covering may include either a high moisture barrier layer, a high oxygen barrier layer, or both. The opaque aluminum foil-containing protective film 55 is provided to prevent penetration of UV and visible spectrum light into the medicament compartment of the container, if such protection is desired.

The alternative high-barrier intermediate laminate film is constructed of a transparent, multi-layer thermoplastic polymer laminate, indicated generally at 71, with high moisture and oxygen barrier properties. In the exemplary embodiment of FIG. 5, the transparent, multi-layer, high-barrier film 71 comprises a sealant layer 72 on its inward facing surface, constructed of 100% polypropylene having a thickness of about 3.0 mils. An oxygen barrier layer 74 is laminated to the sealant layer 72 by a first bond layer 76 comprising a commercially available low density polyethylene (LDPE) extrudate in combination with a primer, and which is interposed between the oxygen barrier layer 74 and the sealant layer 72. Several flexible, polymer films have been determined to be able to provide suitable barriers to oxygen permeability, as will be described further below, but preferably, the oxygen barrier layer 74 of the multi-layer high-barrier film 71 is constructed from a commercially available ethylenevinylalcohol (EVOH) having a thickness of about 0.55 mils.

Ethylenevinylalcohol is primarily noted for its barrier properties against oxygen permeability. In particular, its oxygen permeability barrier values are typically in excess of four orders of magnitude greater than conventional primary bag films such as ethylenevinylacetate (EVA), SURLYN®, medium and high-density polyethylene (MDPE, HDPE). However, while affording a considerable barrier to oxygen permeability, ethylenevinylalcohol, alone, may not provide sufficient protection from water vapor. Accordingly, a moisture barrier layer 78 is laminated to the ethylenevinylalcohol oxygen barrier layer 74 by a second low density polyethylene (LDPE) bonding layer 80. Moisture barrier 78 is a transparent, flexible film comprising an oriented high density polyethylene (oHDPE) polymer available from the Tredegar Co. of Richmond, Va. under the commercial designation of MONAX™, grade HD. The resultant composite barrier structure includes a polyester (PET) heat seal release layer 82 (such as TERPHANE 10.21) on its outward facing surface, and which is laminated, in turn, to the moisture barrier 78 by a third low density polyethylene extrudate bonding layer 84.

The multi-layer, high-barrier polymeric laminate film 71 of the exemplary embodiment described in connection with FIG. 5 is a high oxygen barrier and moisture impermeable flexible film that is suitable for constructing the intermediate layer (64 of FIG. 1) covering the medicament compartment (20 of FIG. 1) of a medical container. All of the materials comprising the laminate are substantially clear and transparent, and do not show any substantial coloration. Thus, the composite film of the illustrated embodiment of FIG. 5 is particularly suitable for covering the medicament compartment of a medical container such that its contents may be readily inspected at a glance.

A higher transparency is obtainable for the multi-layer laminate film 71 of FIG. 5 as opposed to the $SiO_x$ containing laminate film 64 of FIG. 4. In particular, while transparent, the $SiO_x$ containing film exhibits a slight yellowish color, the absence of which in the multi-layer laminate film 71 is thought to be the primary reason for the laminate film's higher transparency.

In addition, $SiO_x$ containing material is relatively rigid and brittle, and can be cracked during the primary container manufacturing, filling, and/or handling process. Because of its inherent rigidity, the barrier properties of a $SiO_x$ containing film decrease if the $SiO_x$ film is stretched beyond 1% due to destruction of the $SiO_x$ film substrate. In addition, the state of $SiO_x$ coating technology is such that a $SiO_x$ film's barrier properties will vary from point-to-point over the surface of the film. This is because currently available $SiO_x$ sputtering processes are not able to form a smooth film of consistent thickness. This variability of barrier properties is typically greater than that shown by extruded polymeric materials, which have a lower variance because of their inherent homogenous character. The barrier properties of a homogenous polymeric barrier film is primarily a function of film thickness, which can be controlled very precisely during the manufacturing process.

While preferred materials for the clear, high-barrier intermediate film would include both an oxygen barrier layer and a moisture barrier layer, alternate materials may be used to provide a medicament compartment cover which is adapted for particular uses. For example, one of the high barrier layers may be omitted giving a high-barrier intermediate film which includes only a moisture barrier layer, or only an oxygen barrier layer. Moreover, the high-barrier intermediate film may include a moisture barrier layer, as described above, in combination with a heat seal release layer which is constructed from a high melting temperature material which also has oxygen barrier properties.

Table 1 is a non-limiting list showing the exemplary film 71 of FIG. 5 and four additional examples of multi-layer films or laminates useful in the fabrication of various embodiments of a clear, high-barrier, intermediate layer according to the invention. In the list, oHDPE refers to an oriented high-density polyethylene such as HD grade MONAX, polyvinylidene chloride coated PET refers to a product available from DuPont Chemical Co. under the commercial designation 50M44, and ACLAR™ refers to polychlorotrifluoroethylene film available from Allied Signal Corporation and which is also known under the commercial designation ULTRX 2000.

TABLE 1

| Material of Laminate Layer 71 | Thickness, mil | Layer Description |
|---|---|---|
| 1. | | |
| PET (outside layer) | 0.48 | Heat Seal Release |
| LDPE Extrudate | 0.5–1 | Bond Layer |
| oHDPE | 2 | Moisture Barrier |
| LDPE | 0.5–1 | Bond Layer |
| EVOH | .55 | Oxygen Barrier |
| LDPE Extrudate/Primer | 0.5–1 | Bond Layer |
| Polypropylene (100%) (inside layer) | 3 | Sealant Layer |
| 2. | | |
| PET | 0.50 | Heat Seal Release |
| Adhesive | | Bond Layer |
| oHDPE | 2 | Moisture Barrier |
| Adhesive | | Bond Layer |
| Polypropylene (100%) | 3 | Sealant Layer |
| 3. | | |
| Polyvinylidene Chloride Coated PET | 0.50 | Heal Seal Release and Oxygen Barrier |
| Adhesive | | Bond Layer |
| oHDPE | 2 | Moisture Barrier |
| Adhesive | | Bond Layer |
| Polypropylene (100%) | 3 | Sealant Layer |
| 4. | | |
| PET | 0.48 | Heat Seal Release |
| Adhesive | | Bond Layer |
| Aclar ™ | 2 | Moisture Barrier |
| Adhesive | | Bond Layer |
| EVOH | .55 | Oxygen Barrier |
| Adhesive | | Bond LAyer |
| Polypropylene (100%) | 3 | Sealant Layer |
| 5. | | |
| Polyvinylidene Chloride Coated PET | 0.50 | Heal Seal Release and Oxygen Barrier |
| Adhesive | | Bond Layer |
| Aclar ™ | 2 | Moisture Barrier |
| Adhesive | | Bond Layer |
| Polypropylene (100%) | 3 | Sealant Layer |

In accordance with practice of the present invention, each of the multi-layer laminate films discussed above, are contemplated as forming a clear high-barrier covering over the medicament compartment 20 of the medical container 10. Preferably, the rear sheet 14 of each such container is constructed of a multi-layer laminate structure including a high moisture barrier aluminum foil-containing film, comprising the 80%/20% wt/wt film on its inwardly facing surface, as described in connection with the embodiment of FIG. 3.

Constructing the rear sheet 14 of the container from an opaque aluminum foil-containing high-barrier laminate film allows the contents of the container to be protected from exposure from UV and visible spectrum light which may degrade its contents. In practical use, the peelable aluminum foil-containing film, covering the medicament compartment, is typically removed prior to dispensing by a hospital's pharmacy. Since the high-barrier intermediate films are clear, they do not provide protection against light exposure and care must be taken to prevent the contents of the medicament compartment from being inadvertently exposed to UV or intense visible spectrum light during subsequent container storage. Accordingly, the container is folded-over upon itself in the region of one of the peelable seals, such that the aluminum foil-containing film (or rear sheet) forms the outward facing surface of the folded-over container and helps protect the contents of the medicament compartment from exposure to UV or intense visible spectrum light.

Turning to FIG. 6, the container 10 is shown being folded over along the line of one of the peelable seals or in advance of one of the peelable seals. When so folded, the material of the front and rear sheets of the bag is pinched together by the fold thereby imparting additional protection to the seal. The fold provides additional resistance to hydraulic pressure caused, for example, by inadvertently squeezing the diluent compartment of the bag.

In accordance with preferred embodiments of the present invention, means are provided to secure the container in a folded-over condition so as to guard against accidental activation and to help protect the container's contents from radiation exposure by allowing only the aluminum foil-containing rear sheet to be exposed to ambient light.

Referring now to FIGS. 1 and 6, means for maintaining the bag in a folded-over condition suitably comprises a locking tab 28 formed of the primary bag material and extending from one side of the container, and a matching engagement slot 27, configured to receive the tab 28 when the bag is folded-over along a line in the region of the first peelable seal 24 between the diluent and medicament compartments. Once the container is folded-over, and locking tab 28 is engaged with matching slot 27, the contents of the medicament compartment are protected on both sides from incident radiation, by the aluminum foil-containing rear sheet.

Accordingly, it will be understood that configuring the bag in a folded-over condition assists in providing protection for the contents of the medicament compartment from radiation degradation while also protecting against inadvertent bag activation by increasing the strength of the peelable seal along which the bag is folded. In addition, the means for maintaining the bag in a folded-over condition is adaptable to easy engagement and disengagement, thus allowing the clear inside face of the medical container to be periodically exposed and allowing the contents of the medical container to be periodically accessed for visual inspection of compartment integrity.

Figure 7:
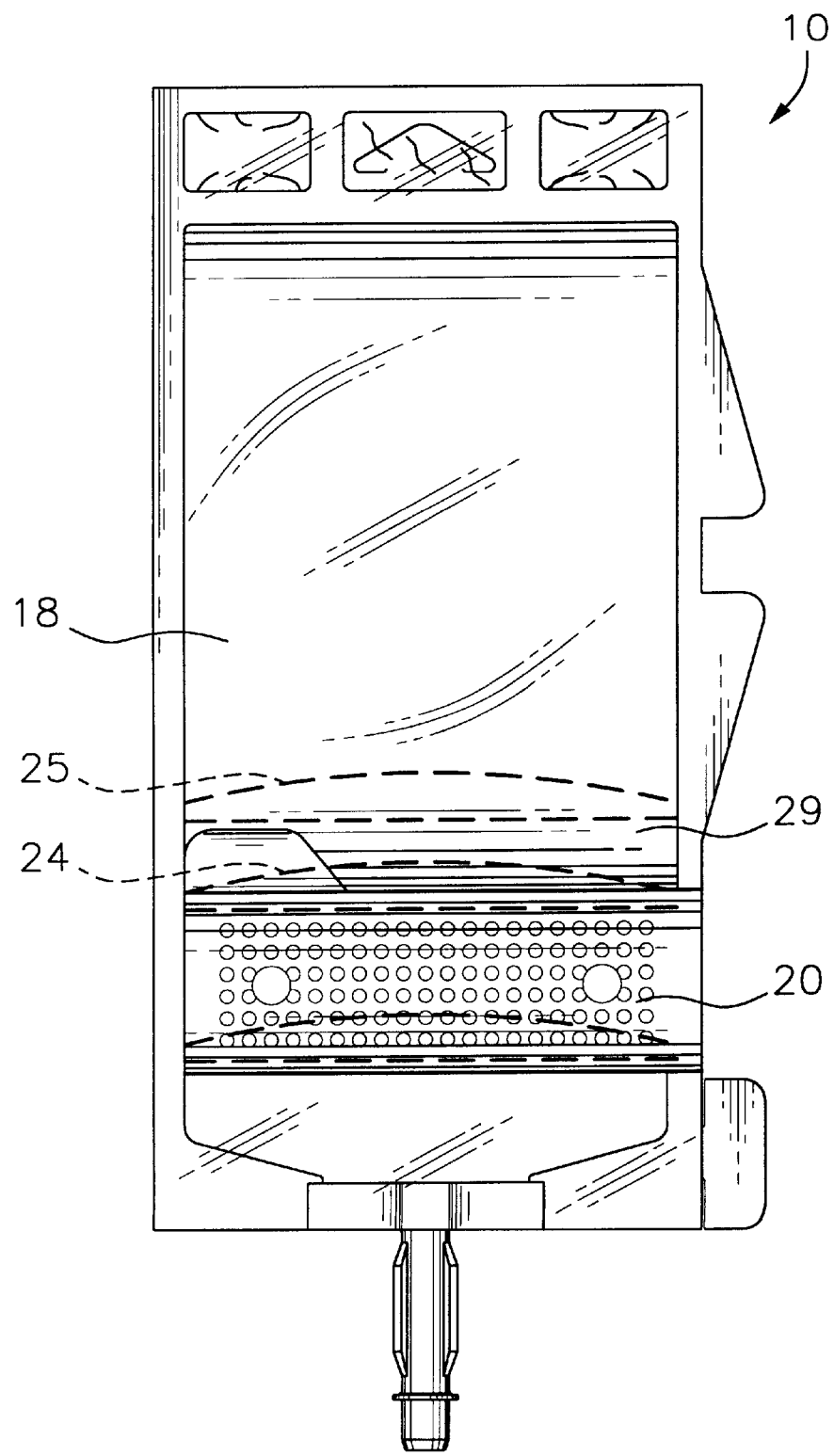
FIG. 7 is a semi-schematic front view of an additional embodiment of the container provided in accordance with the present invention showing an additional peelable seal and buffer compartment provided for protecting the medicament compartment against moisture vapor permeation.

Referring to FIG. 7, in an exemplary embodiment, additional protection is provided to the medicament compartment by providing a sacrificial moisture vapor permeation path for moisture vapor which may be developed in the liquid-containing diluent compartment. The sacrificial moisture vapor permeation path is provided by forming an additional peelable seal 25 across the medical container a short distance in advance of, or above, the peelable seal 24 which separates the medicament compartment from the diluent compartment. The additional peelable seal 25 is preferably disposed about ⅛ to ½ inch above the peelable seal 24, i.e. in the direction of the diluent compartment 18. The first peelable seal 24 and the additional peelable seal 25, together define a buffer compartment 29, disposed between the diluent compartment 18 and the medicament compartment 20. The buffer compartment 29 is preferably empty.

When the medical container is constructed with the additional peelable seal 25 and buffer compartment 29, a sacrificial moisture vapor permeation path is provided which protects powdered drugs in the medicament compartment 20 from moisture permeating through the container material from the diluent compartment. Although the medicament compartment 20 is covered by one of a variety of high-barrier protective coverings, as described above, a path exists, for moisture to migrate from the diluent compartment to the medicament compartment, through the primary container materials comprising the first peelable seal 24. In the embodiment of the invention depicted in FIG. 7, moisture vapor which may permeate through the primary container materials in the region of the additional peelable seal 25, from the diluent compartment is trapped within the buffer compartment 29. Since the surface area of the buffer compartment 29 available for vapor permeation is much larger than the permeation surface provided by the peelable seal 24, moisture vapor in the buffer compartment will preferentially escape into the atmosphere, rather than migrate through the material of the first peelable seal 24 and into the medicament compartment.

Thus, it can be seen that the additional peelable seal 25 and buffer compartment 29 provides means for protecting the dry medicament in the medicament compartment from being degraded by moisture.

Manufacture and Assembly of the Container

In accordance with practice of principles of the invention, the front 12 and rear 14 sheets of one exemplary embodiment of the container 10 interface to one another by an 80:20 film layer. Although other interfacing films are within the scope and contemplation of the invention, in each of the embodiments described above, the inward facing layer of the front sheet 12 comprises an 80:20 film, which is placed in contact with the inward facing 80:20 film layer of the back sheet 14.

The composition of the front and rear sheets 12 and 14 of the container 10, allow for the creation of the peripheral seals and peelable seals using heat sealing techniques. Hot bars or dies are used at differing temperatures, pressures and application times to bring interfacing portions of the materials and laminates employed to temperatures near or above their melting points to allow migration of material across the interface to thereby form a bond of the desired strength and characteristics.

For either a single layer film, or a multi-layer laminate film, comprising the front sheet 12 and the aluminum foil laminate comprising the rear sheet 14, a procedure for fabrication of the container 10 of the illustrative embodiment, is described in connection with FIG. 8. The procedure comprises cutting the front and rear sheets of the container to the desired vertical container dimensions, but oversized in the horizontal dimension.

If the container 10 is being constructed with a single layer front sheet 12, the high-barrier aluminum foil-containing protective layer 55 (of FIG. 3) and the transparent high-barrier intermediate layer (64 of FIG. 4 or 71 of FIG. 5), comprising the high-barrier covers for the medicament compartment 20 are cut to size, positioned over the area which will become the medicament compartment, and sequentially attached to the container's front sheet 12. In accordance with the invention, the transparent high-barrier intermediate layer is first laminated over the surface of the front sheet, and the aluminum foil-containing protective layer 55 overlaid thereto.

Specifically, the transparent high-barrier intermediate layer 64 or 71 is positioned over the medicament compartment and held in place by a pair of rods while it is being laminated onto the surface of the front sheet 12. The portion of the layer in contact with the rods is, thus, not accessible to, for example, the heat seal head, resulting in a small portion of the film not being sealed onto the surface of the front sheet. The residue of the use of rods to secure the transparent high-barrier intermediate layer in position results in a non-sealed area having the contact footprint of the rod. In the embodiment illustrated in FIG. 1, the rod contact surface is generally circular and results in two circular non-sealed regions 41 which remain visible because of the reverse imprinting caused by pressure applied during the sealing process.

Following lamination of the intermediate layer 64 or 71, the aluminum foil layer 55 is applied over the surface thereof, using a patterned heat sealing die as described above.

Following attachment of the aluminum foil layer 55 and the transparent high-barrier layer 64 or 71, the front and rear sheets are mated together and the outlet port 30 is inserted in its desired final position between the front and rear sheets. The outlet port 30 of the illustrated embodiment, is injection molded and has a composition of 40% FINA Z9450 polyethylene-polypropylene co-polymer and 60% Shell KRATON™ G1652 styrene ethylene-butylene styrene thermal plastic elastomer. Following insertion of the outlet port, a heated die is employed to create a seal between the outlet port flanges 34 and the lower edge of the front and rear sheets adjacent the flange.

The peelable seals 24 and 26 (and optionally the additional peelable seal 25) dividing the compartments and the container 10 are then created using, for example, double hot bars comprising a front bar in alignment with a rear bar constraining the elements of the container therebetween to form the seal thereby. In an exemplary embodiment, the front bar which contacts the previously combined high-barrier protective film 55, intermediate films 64 or 71, and front sheet 12, is maintained at a temperature in the range of about 245° F. to about 265° F. The rear bar which contacts the rear sheet 14 is maintained at substantially the same temperature as the front bar (in the range of about 245° F. to about 265° F.) and may optionally include a thin rubber coating to assure uniform application of pressure. The double bars are pressed into contact with the front and rear sheets with a pressure in the range of from about 230 psi to about 340 psi and maintained at that temperature and pressure for a period of time between about 1.5 to about 2.5 seconds. The peelable seals 24 and 26 as shown in FIG. 2 may be made individually with a single double bar set up, or simultaneously with a twin double bar set up. The additional peelable seal 25 may be easily accommodated by a triple double bar set up.

A further refinement to the above-described embodiment of peelable seal formation, involves configuring a heat seal head with a double seal bar configuration in which one end of the double bars are connected together by a transverse seal bar so as to describe a square-cornered, elongated U shape. When such a seal head is pressed into contact with the front and rear sheets and maintained at the temperature and pressure regime described above, an additional peelable seal 25 is provided which spans the transverse peelable seals 24 and 26 and is disposed adjacent and parallel to the permanent peripheral seal 16 which is formed along the edge of the container opposite the sacrificial ports. This additional seal 25 is preferably formed when the container is manufactured to include a high-barrier protective film disposed over the surface of the medicament compartment.

In such a case, the material thicknesses experienced by a heat seal head will be different (thicker) in the region defined by the medicament compartment 20 than the region defined by the material comprising the permanent peripheral seal 16. The difference in material thickness between these two regions requires that the heat seal head exert pressure against a conformal backing, such as rubber, in order to ensure uniform seal pressure across the interface. Forming the additional peelable seal 25 within the periphery of the medicament compartment, obviates the requirement for a conformal backing for the seal head. The material thickness experienced by the heat sealer will thus be constant, ensuring a uniform, leak resistant peelable seal.

Following the formation of the peelable seal, the front and rear sheets are mated together by a peripheral permanent heat seal 16 which extends across the top, bottom, and along one continuous side of the container, in a manner such that it overlaps a portion of the peelable seal 25 which spans the transverse seals 24 and 26, thus ensuring leak proof seals between the diluent, medicament and lower compartments. As is best seen in FIG. 8, on the opposite side of the container, the permanent seal 16 is spaced-away from the oversized edge of the front and rear sheets and is provided in broken-fashion along the desired edge of the final bag, i.e., the seal is formed along the top vertical portion 110a, a bottom vertical portion 110b, and a central vertical portion 110c, thus defining intervening spaces between the three vertical portions.

Sacrificial ports 102 and 104 are inserted between the front and rear sheets in positions along the edge of the oversized portion thereof adjacent the gaps in the permanent heat seal. In a manner similar to the outlet port 30, the front and rear sheets are sealed to the sacrificial ports 102 and 104 along tapered flanges 106 and 108, respectively, provided for such purpose. The sacrificial ports 102 and 104 are also injection molded and because they will be removed and disposed of at a later stage in the process, are constructed from any inexpensive thermoplastic material available. In particular, the sacrificial ports may be constructed of 80:20 film "regrind" material, simple polypropylene, or the like.

Figure 8:
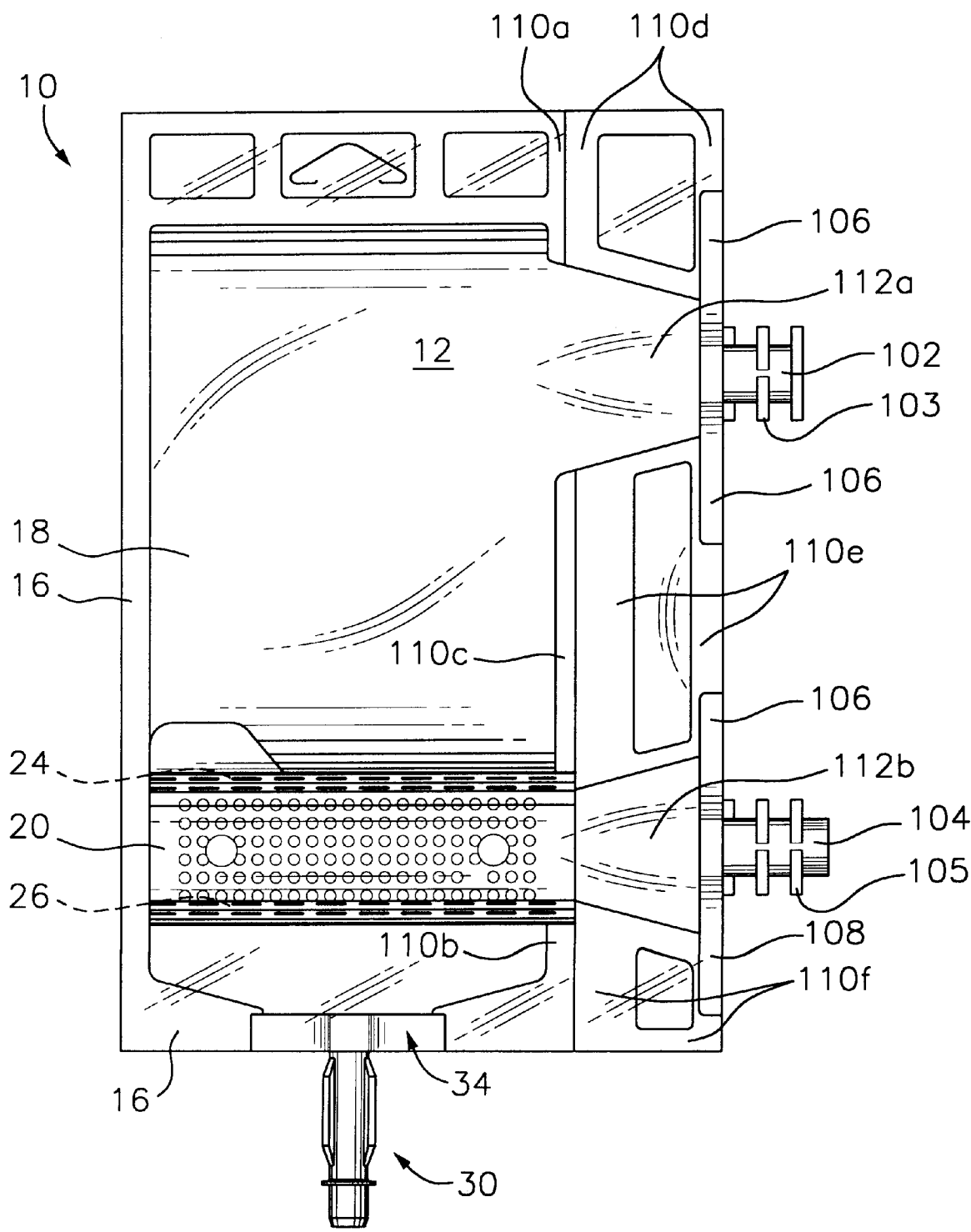
FIG. 8 is a semi-schematic front view of an exemplary embodiment of a container provided in accordance with the present invention at an intermediate stage of its fabrication showing the arrangement of sacrificial ports for filling of the container.
Figure 8B:
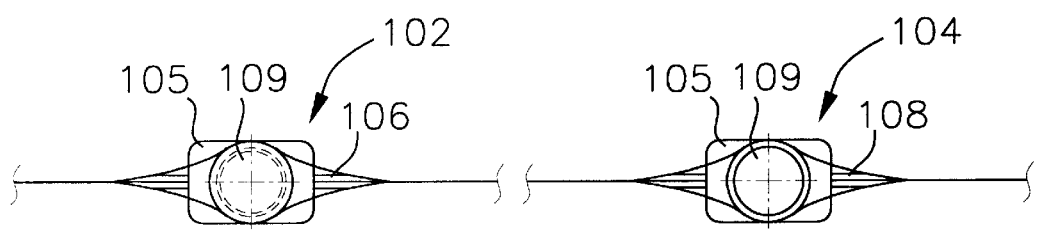
FIG. 8b is a semi-schematic top view of the sacrificial ports of FIG. 8a detailing the shape and arrangement of the port flanges.
Figure 8A:
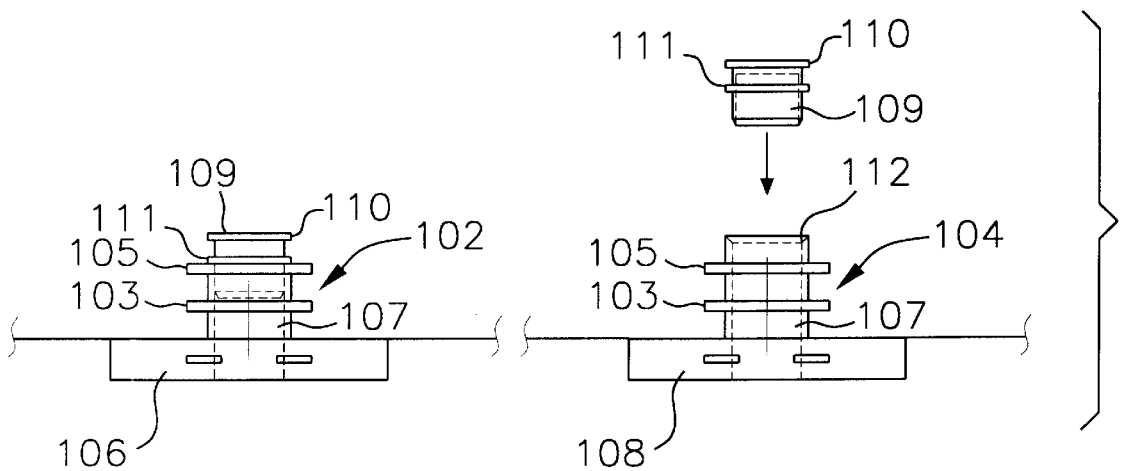
FIG. 8a is a semi-schematic side view of an exemplary embodiment of a container, detailing the arrangement and construction of the powder and liquid fill sacrificial ports including a cap in accordance with the present invention.

The sacrificial ports 102 and 104 depicted in greater detail in FIGS. 8a and 8b, with FIG. 8a depicting the diluent filling port 102 and powder filling port 104, respectively, in side view and with FIG. 8b depicting the ports in semi-schematic plan view. The sacrificial ports 102 and 104, respectively, include a cap 109 which has been inserted into the diluent filling port 102 and is depicted as suspended above the powder filling port 104.

The sacrificial ports 102 and 104 are an important feature of the present invention and, as will be described further below, provide a means for aseptically filling a single or multiple compartment container with powdered medicaments, liquid diluents, and the like. In addition, the sacrificial ports are provided with structure to allow the ports and, thereby, the medical container to be supported and manipulated by automated robotic machinery.

As is depicted in FIG. 8a, the sacrificial ports 102 and 104, each includes two vertically spaced-apart flanges, a lower flange 103 and an upper flange 105. Each of the flanges are generally rectangular in shape (best seen in FIG. 8b), with their long edges extending approximately 3 mm, to either side, beyond the generally tubular barrel 107 of each respective sacrificial port. As can be seen in FIG. 8b, each flange's short side (or width) has the same dimension as the outer diameter of the port's generally tubular filling barrel (12 mm). Each of the flanges 103 and 105 is constructed with a thickness of approximately 1.5 mm, and are placed in vertical, spaced-apart relationship with each other and with the intersection of each port's barrel with its respective tapered flange (106 and 108). The bottom most flange 103, on each port, is positioned approximately 4 to 5 mm above the intersection of the port barrel and the port's tapered flange, while the uppermost flange 105 is positioned such that its bottom surface is approximately 4 mm above the top surface of the bottom flange 103, thus defining an approximately 4 mm spacing between the flanges and between the bottom flange and the container edge.

In accordance with practice of principles of the invention, the generally tubular barrel 107 of each sacrificial port 102 and 104 has an outer diameter of approximately 12 mm and a length, or height depending on whether it is a diluent filling port 102 or a powder filling port 104. In the case of the diluent port 102, in one exemplary embodiment the barrel has a height of about 13 mm, and in the case of the powder filling port 104, the barrel has a height of about 18 mm. It will be understood by those having skill in the art, that the inner and outer diameters of the filling barrel are generally the same as those of a conventional glass or plastic drug vial. This configuration allows the filling barrels of the sacrificial ports to be accessed by conventional drug vial filling apparatus.

Each of the generally tubular barrels is provided with a through-bore, thus defining a cylindrical shape. In an exemplary embodiment, the diameter of each through-bore is approximately 10.4 mm, thereby giving a cylindrical sidewall thickness of about 0.8 mm. The upper edge of each barrel has a chamfer provided at about a 45° angle towards the interior of the barrel.

A generally cylindrical cap (or plug) 109 is provided for each of the ports and is constructed with an outer diameter (10.5 mm) which is slightly larger than the inner diameter of each port's filling barrel (10.4 mm), such that when the cap 109 is inserted into a port, the interface between the cap outer diameter and the port inner diameter provides a hermetic seal. This seal is required to prevent particulates from entering the container before filling and for preventing powdered medicaments or liquid diluents from escaping after the container has been aseptically filled. As can be seen in FIG. 8a, the bottom edge 109a of the cap 109 is beveled at about a 45° angle, so as to engage the 45° chamfer of each port's barrel and aide in insertion.

In addition to the flanges 103 and 105 on the ports, a pair of vertically spaced-apart flanges are also provided on the cap. In the exemplary embodiment of FIG. 8a, a generally circumferential upper flange 110 defines the top of the cap and has a thickness of about 1.0 mm and a diameter of about 12.0 mm so as to extend beyond the cap body by about 0.75 mm. The upper flange overhang thus allows a "lifting" mechanism to engage the underside of the upper flange 110 and provide a means to lift the cap vertically out of its respective port barrel. A lower flange 111 is provided in order to control the insertion depth of the cap when the cap is inserted into the port barrel or reseated after a filling operation, for example. The lower flange 111 may be fully circumferential or, alternatively may be implemented as a partial flange defining a simple lateral extension from the body of the cap. As was the case with the upper flange 110, the lower flange 111 has a thickness of approximately 1 mm and is constructed to extend outwardly from the body of the cap by about 0.75 mm. The upper and lower flanges 110 and 111 are vertically spaced-apart from one another, along the body of the cap, so as to define an approximately 3 mm space therebetween.

Accordingly, it will be seen that following insertion, each cap 109 adds approximately 5 millimeters to the overall height of their respective sacrificial port. It will also be noted that the diluent port 102 and cap combination has a height of 18 millimeters, which is the same as the height of the medicament port 104 without its cap having been inserted. This particular feature allows the cap to be removed from the medicament sacrificial port 104 and the container to be indexed beneath a conventional, rotary powder-filling mechanism, while allowing the diluent compartment's port to remain sealed. Maintaining the sealed diluent compartment's port at a height equal to or less than the height of a medicament compartment's port in the unsealed condition allows both ports to pass beneath and clear a powder wheel while being indexed in an efficient, in-line fashion.

Returning now to FIG. 8, the permanent seals 110*a*, 110*b*, and 110*c*, are next extended towards the oversized edge of the container by seal extensions 110*d*, 110*e*, and 110*f* respectively. These seal extensions are formed with a suitable width to allow the oversized container portion, including the sacrificial ports, to be cut away from the filled container after the manufacturing process has been completed without the danger of substantially weakening the container's peripheral seal along the cut-away edge.

In particular, oversized portions 110*e* and 110*f* have a width sufficient to enable the retaining slot (27 of FIG. 1) and the retaining tab (28 of FIG. 1) to be cut from the relatively stiff material of the seal extensions 110*e* and 110*f* respectively.

The seals, and seal extensions, formed in the oversized portion of the container, define voids or channels 112*a* and 112*b*, in the intervening container material between the seals. The channel 112*a* allows communication between the sacrificial port 102 and the interior of the diluent compartment 18, while the channel 112*b* allows communication between the sacrificial port 104 and the open medicament compartment 20. As will be described further below, the channels 112*a* and 112*b* are closed-off by a subsequent permanent heat seal which links the various spaced-apart vertical seal portions (110*a–f*) on the oversized portion of the container.

Container Fabrication Apparatus

In accordance with practice of principles of the present invention, a procedure and apparatus for fabricating the container 10 of FIG. 8, will now be described in connection with FIG. 9. As will be evident from the following description of a container fabrication apparatus, both the apparatus and procedure are adapted to be suitable for manufacturing medical containers with front and rear sheets comprising either single layer or multi-layer laminate films. In addition, it will be evident from the following description that the number, shape, configuration and location of the various seals of the container 10 of FIG. 8, can be easily changed, or indeed even omitted, due to the modular arrangement of components of the apparatus.

Figure 9:
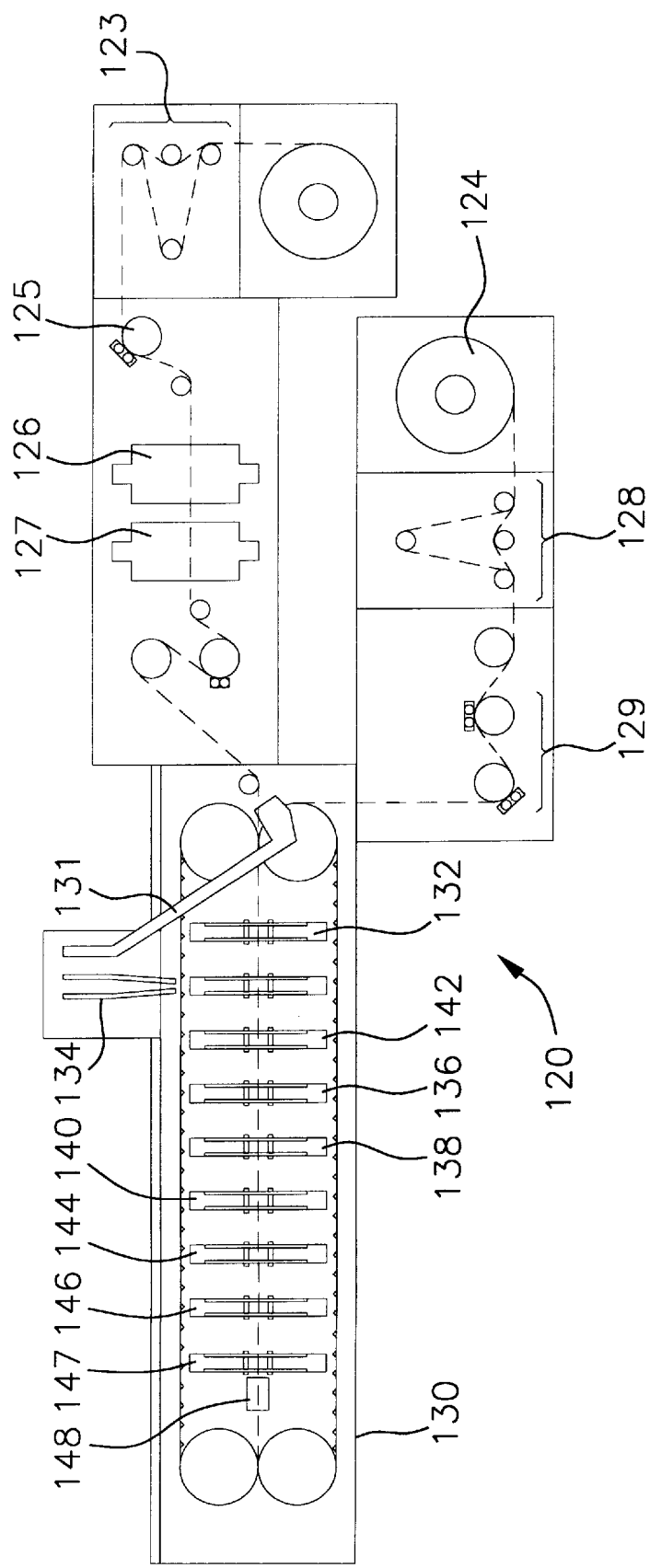
FIG. 9 is a semi-schematic plan view of an embodiment of a modular container fabrication apparatus in accordance with the present invention.

FIG. 9 is a semi-schematic plan view of an exemplary embodiment of a container fabrication machine 120 provided in accordance with the present invention, showing the arrangement and positioning of various seal forming stations and the arrangement and configuration of the container primarily film web supply rolls.

Bulk material for the container front and rear sheets (12 and 14 of FIG. 2, for example) is provided to the container fabrication machine 120 in the form of respective bulk film web supply rolls, 122 and 124, which are mounted at web supply roll stations at the intake end of the container fabrication machine 120. Web material from the, for example, front sheet supply roll 122 is threaded through a dancer station 123, which functions to maintain the web material at a proper tension as the web is drawn through the remaining stations of the fabrication machine 120. Following dancer station 123, the web material is transported by vacuum feed wheels past a first web cleaning station 125 and next through a series of optional barrier film application stations 126 and 127, disposed serially along the web path. If the container (10 of FIG. 1) is being constructed in the manner described previously, i.e., to include a single layer front sheet 12, a transparent high-barrier intermediate film (64 of FIG. 4 or 71 of FIG. 5) and a high-barrier aluminum foil-containing protective layer (55 of FIG. 3), the high-barrier covers for the medicament compartment 20 are first cut to size, next positioned over the area which will become the medicament compartment, and then sequentially attached to the container's front sheet in the barrier film application stations 126 and 127 respectively. In accordance with the invention, transparent high-barrier intermediate layer is first laminated over the surface of the front sheet in application station 126 and the aluminum foil-containing protective layer overlaid thereto in application station 127.

In like manner, web material which will form the container rear sheet is threaded from its respective bulk web supply roll 124 through a corresponding dancer station 128; and is transported by vacuum feed wheels through a corresponding web cleaning station 129.

When the continuous film of front and rear sheet web material leaves their respective preparation stages, the continuous films are fed into registration with one another and are oriented such that the 80:20 surfaces of each continuous film faces the 80:20 surface of the other. Once the continuous film webs have been put into registration, the web material is continuously indexed and longitudinally moved through the seal core 130 of the fabrication apparatus 120. Sacrificial diluent and medicament ports are located along the web sandwich and positioned between the front and rear sheet film webs, and various seals are sequentially formed on the web sandwich material so as to join the webs together and substantially fabricate the container into an intermediate stage suitable for aseptic filling.

In accordance with practice of principles of the invention, the fabrication machine seal core 130 comprises a multiplicity of seal presses and port insertion stations, arranged in series fashion along the travel path of the container film web sandwich. The first such station is a set port loading station 131, in which a set port, or outlet port (30 of FIG. 8) is inserted in its proper position between the front and rear sheets. A heated press, including a shaped die, is compressed over the web material to create a seal between the outlet port flange (34 of FIG. 8) and the eventual lower edge of the front and rear sheets adjacent the flange, at set port seal station 132.

The set, or outlet, port 30 is comprised of a plastic material and is injection molded from a composition of 40% FINA Z9450 polypropylene co-polymer and 60% Shell KRATON G1652 styrene ethylene-butylene styrene thermal plastic elastomer. Because of the similarities between the material composition of the set port 30 and the material of the inner, seal-forming surfaces of the front and rear sheet, it can be seen that the front and rear sheets may be sealed to the set port flange 34 using a substantially similar heat seal regime, as that used for the formation of the permanent, peripheral seals, to be described in greater detail below.

Following insertion and sealing of the set port 30 to the container material, the film web sandwich is next indexed to a sacrificial port insertion station 134, at which sacrificial ports (102 and 104 in FIG. 8) are inserted between the front and rear sheets, in positions along the respective sides of the container portions which will become the diluent 18 and medicament 20 compartments. Sacrificial ports 102 and 104 are preferably injection molded from a 100% polypropylene material but may also be fabricated of a material having a composition similar to the composition of the outlet port 30. In a manner likewise similar to the outlet port 30, the front and rear sheets are sealed to the sacrificial ports 102 and 104 along tapered flanges 106 and 108, respectively, which are provided for such purpose.

Following insertion of the sacrificial ports 102 and 104, the front and rear sheet film material is mated together by a permanent peripheral heat seal (16 of FIG. 8) which extends across what will become the top, bottom, and one continuous side of the finished container. Along the opposite side of the container, the permanent heat seal 16 is provided parallel to, but spaced-away from, the edge of the film web sandwich strip, and is formed in broken-fashion along the desired edge of the finished container (110a and 110b and 110c of FIG. 8).

Following formation of the perimeter seal at the perimeter seal station 136, the container material is indexed to a first, optional, medicament sacrificial port seal station 138. The front and rear sheet material is sealed to the tapered flange 108 of the medicament sacrificial port 104 by compressing the front and rear sheet material to the tapered flange of the port by a pair of concave conformal heated sealing dies. As was the case with the set port die, the heated sealing die of the medicament seal station 138 is conformally shaped such that when the two halves of the sealing die are compressed together, they form a generally elliptical pocket having a shape which is the mirror image of the convex tapered sealing surface of the medicament port.

Next, the web material is indexed to a second, optional, diluent compartment sacrificial port seal station 140, where the front and rear sheet material of the container is compressed and heat sealed to the tapered flange 106 of the medicament compartment sacrificial port 102.

It will be appreciated that the order of sealing the sacrificial ports to the container is purely arbitrary and that the medicament port seal station 138 may just as easily follow the diluent port seal station 140 as vice versa. In addition, the seal stations for sealing the sacrificial ports to the container may precede perimeter seal station 136. In addition, a further optional seal station, peelable seal formation station 142 which is depicted in FIG. 9 as following the sacrificial port insertion station 134 and preceding the perimeter seal station 136, is optionally provided to form peelable seals which bisect and subdivide the container 10 into a plurality of compartments. Alteratively, the optional peelable seal station 142 may be configured to proceed the sacrificial port insertion station 134, by merely repositioning the peelable seal station along the film web path. It will be evident as well, that a multiplicity of peelable seal stations may be provided, if the container is to be fabricated with multiple compartments.

It should be evident to one having skill in the art, that the sequential, but independent, plurality of seal stations may each be configured to operate automatically as the film web is indexed to their respective stations. Alternatively, the seal stations may be present in the container fabrication machine, but rendered inactive, such that their particular seals are not formed on a specific production run.

Following the sacrificial port seals, the container web material is indexed to a trim zone sealing station 144, which applies a permanent heat seal to the container material which contacts and overlaps the broken portion of the permanent perimeter seal and extends to the edge of the container film material. The trim zone seal regions (110d, 110e and 110f of FIG. 8) are provided in the film region between the container peripheral seal and the web edge so as to define a relatively low-flexibility region of material having a width sufficient to enable the retaining slot (27 of FIG. 1) and the retaining tab (28 of FIG. 1) to be trimmed out of the relatively stiff material of the trim zone seals. In addition, the trim zone seals function to add width to the peripheral seals (110a, 110b, and 110c) such that the perimeter seals in this region are formed with a suitable width to allow this region of the container (including the sacrificial ports) to be cut away from the container after the manufacturing and filling processes have been completed, without substantially weakening the container's peripheral seal along the cut-away edge and endangering the filled container's integrity.

As can be seen from FIG. 8, the trim zone seals 110d, 110e, and 110f, define voids or channels 112a and 112b, in the intervening container material between the seals. Channel 112a thus allows communication between the sacrificial port 102 and the interior of the diluent compartment 18, while channel 112b allows communication between the sacrificial port 104 and the medicament compartment 20, allowing both compartments to be accessed through their respective sacrificial ports. As will be described further below, the channels 112a and 112b are closed-off by a subsequent permanent heat seal which links the trim zone seal portions (111a–f) in these regions of the container.

Following the heat seal process steps, the container is indexed through a hanger punch station 146, which forms a hanger cutout of the top center of the container. Following stations 147 and 148 separate the containers by cutting the material web at first the port end (147): a top trim station 148 cuts away the container material at the hanger end following which the container is unloaded from the fabrication machine 120 and container construction is substantially complete.

It will be evident to one having skill in the art that the number and configuration of compartments comprising the container is determined solely by the number and location of the various heat seals used to form the container. In addition, depending on the number of containers contemplated for the final product, a suitable number of sacrificial ports are provided and positioned along their respective material web edges. It will be understood that the modular manufacturing process according to the present invention is adaptable to manufacture medical containers having a single primary compartment, or multiple compartment containers having any number of compartments, by merely providing additional peelable seals and additional sacrificial ports with which to fill the compartments. For each configuration of compartments and sacrificial ports, the trim zone seal press at trim zone seal station 144 may be suitably reconfigured by removing one press face and substituting another, which is configured to provide one, three, four or the like channels or openings so as to connect a plurality of sacrificial ports to a plurality of compartments.

In similar fashion, it will be clear to one having skill in the art that the composition of the container front and rear sheets may be changed by suitably replacing the front and rear sheet film supply web rolls with other suitable materials. In particular, both the front and rear sheet supply rolls may be single layer 80:20 film such that the finished container is transparent on both sides. Because of the modular nature of the fabrication apparatus, the clear barrier application station and the foil barrier application station may both be rendered inoperable, as well as the peelable seal formation station, thus configuring the container fabrication machine to provide a single-compartment container which is completely transparent, and which may comprise a multiplicity of outlet ports, such as separate med ports and set ports.

Accordingly, the container fabrication machine in accordance with the present invention is seen as being suitable for manufacturing a wide variety of medical containers, having a wide variety of sizes, and a variety of seal configurations and port locations. All of the containers so manufactured will be seen to be suitable for aseptic filling in accordance with practice of principles of the invention as well as suitable for use in combination with a terminal sterilization procedure, if such is desired.

Seal Formation

The peelable seals formed during the manufacturing process described above are straight-line seals which have a thin, rectangular shape. While they appear similar to conventional straight-line seals, the peelable seals of this embodiment are improved in that they exhibit a more predictable rupture characteristic across production lots, i.e., they exhibit a uniform resistance characteristic to manipulation pressure.

Without being bound by theory, it is thought that the peelability of the seals is attained by limiting the time, pressure and temperature to that necessary to fuse the interface between the inner layers of the front and rear sheets which have a lower melting temperature than the intermediate and outer layers of the rear sheet. The depth of the structural alteration in the inner layers in the fusion zone is limited, thereby imparting the peelable character to the seal while providing sufficient strength to prevent breakage in normal handling of the container.

Preferably, the activation force for the container of the present invention is tightly controlled to provide container integrity under extreme handling conditions, yet be easy to activate for all users. This activation effort or force is characterized by a burst pressure which is preferably approximately 4±1 lbs. pounds per square inch (psi).

In order to achieve such uniformity in the burst pressure of a generally rectangular seal, it has been determined that the critical parameter which must be controlled is temperature. Uniform burst pressure response is achievable by controlling the seal temperature to within ±2° F. Commercially available production heat seal apparatus are not able to control the variability in heat seal temperature to this desired range. However, the heat seal time is able to be controlled very precisely. Accordingly, time is chosen as the control parameter and adjusted to compensate for the variation in heat seal temperature. Time and pressure of the seal head are monitored to ensure that they are within acceptable ranges as described above and the heat seal time is adjusted accordingly. While the contact pressure is preferably in the range of from about 230 psi to about 340 psi, it will be recognized by one having skill in the art that the lower figure in the range (about 230 psi) is provided for convenience in setting the parameters of a production heat seal machine. So long as the pressure exerted by the heat seal bars on the container material is sufficient to force the material seal layers into contact over the surface area of the desired seal, a peelable seal will be formed given an appropriate temperature and time. Indeed, it has been experimentally determined that variations in heat seal temperature and time beyond those contemplated by the present invention result in seals that not only fail to exhibit the desired uniform resistance characteristic, but also fail to rupture completely along the length of the seal. Incomplete seal rupture often results in residual diluent, for example, remaining trapped in 90° corners where the peelable seals contact the permanent peripheral seals of the container. Accordingly, the diluent/medicament mixture ratio may not be as designed, and drug delivery may be at a higher concentration than desired.

Examples of specific time, temperature and pressure settings which will form peelable seals, in the 80:20 film of the illustrated embodiments, having a burst pressure of about 4±1 psi include: pressure 235 psi, temperature=257° F., and time=1.9 seconds; and pressure=235 psi, temperature=263° F., time=1.75 seconds.

Higher temperatures and associated pressures and times are used to provide the peripheral permanent heat seals and the outlet port seal, which produce structure altering effects in a greater proportion to, or depth of, the sealing layers. Such seals may be formed by heat sealing at a temperature of 290° F. and a pressure of up to 200 psi for about two seconds. Those skilled in the art will recognize that various techniques for forming both permanent and peelable seals may be used in the construction of the container of the present invention. In particular, it will be evident that controlling seal temperature to a greater degree (to within about ±2° F.) will also allow formation of peelable seals having uniform burst pressure. In addition, time is chosen as the control parameter for seal formation because it is able to be precisely controlled. Precision control of temperature, pressure, or both would give the same result.

Moreover, those skilled in the art will recognize that the sequence for constructing the container 10 of the present invention is arbitrary and has been defined to accommodate a particular production process and a particular embodiment of the final container. Various alterations in the order of formation steps, as well as the positioning and orientation of the various components comprising the container 10 may all be modified without parting from the principles of the present invention.

After the container is brought to the stage of fabrication exemplified in FIG. 8, the container is now in a condition for aseptic filling with a medicament, a diluent, both or any desired combination of the foregoing. In an exemplary filling process, the particular embodiment of the container to be filled, in accordance with the invention, is one which incorporates either a single layer or multi-layer laminate front sheet film and a multi-layer aluminum foil laminate rear sheet film and has been formed to comprise a diluent compartment 18 and medicament compartment 20, both of which have peripheral edges left unsealed for filling through respectively provided sacrificial ports 102 and 104. This embodiment of the container is at the stage of fabrication as is depicted in FIG. 8. Primary container fabrication, including the provision of an outlet port and sacrificial ports, is accomplished by the method and apparatus described previously.

In order for an aseptic filling process to be acceptable for medical purposes, the container to be filled must be provided in a sterile condition. Conventionally, container sterilization takes place in a separate processing area or facility due to the rather extensive and complex equipment and processes required for sterilizing material. A particular undesirable feature of the sterilization procedure is that the container must be transported to the sterilization facility for processing, following which container sterility must be maintained during subsequent storage and transport to an aseptic filling facility. The container must be introduced into the aseptic filling zone by means of a sterile transfer in order to prevent contamination of the aseptic zone by the container. Once introduced into the aseptic zone, the container may be filled aseptically, but must be further handled in a sterile fashion.

In accordance with practice of principles of the invention, following primary container fabrication, a plurality of empty containers are loaded into a handling container which is then sealed to protect the bags contained within from environmental contamination.

Figure 10:
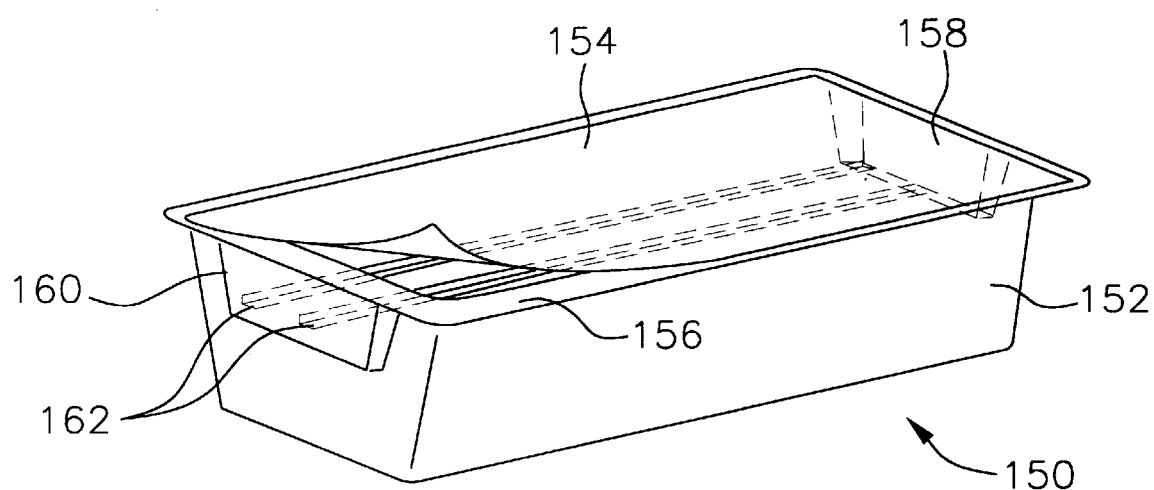
FIG. 10 is a semi-schematic perspective view of a handling container provided in accordance with the present invention, including a container tray for receiving a rail cartridge and covered by a sealable film lid.

Turning now to FIG. 10, a handling container, generally indicated at 150 and termed "a carrier" herein, functions as a transportable sterile containment isolator for sterilizing, transporting and introducing into the aseptic zone, empty containers in a systematic manner. The carrier 150 comprises three components; a generally rectangular container tray 152, a sealable film lid 154, and a rail cartridge 162 for supporting a multiplicity of containers within the tray and which will be described in greater detail below in connection with FIGS. 11a & 11b.

The generally rectangular container tray 152 is constructed of a thermoformed polystyrene material chosen to be able to withstand several sterilization cycles without significant degradation. The tray 152 is shaped generally in the form of a basin with its upper peripheral edge bent-over outwardly to form a flat, horizontally oriented peripheral lip 156 which extends beyond the sides of the tray 152 for a distance of between about ¼ inch to about 1 inch. Preferably, the lip 156 extends about ¾ inch beyond the sides of the tray, but any extension which provides rigidity to the tray 152 and a sufficient surface to support a seal is suitable. Two opposing pockets 158 and 160 are formed in about the centers of the two opposing short sides of the tray and extend outward from the plane of the short sides. The pockets 158 and 160 extend only partially downward along the sides of the tray and form, thereby, two opposing recesses into which the ends of the rail cartridge 162 may be inserted. The rail cartridge 162 rests on the bottom surfaces of the pockets 158 and 160 and is thereby suspended above the bottom of the tray 152 at a height sufficient to allow containers arranged on the rail cartridge to hang free within the interior volume of the tray. Accordingly, the pockets 158 and 160, in combination with the rail cartridge 162, functions to maintain a multiplicity of containers in a specific orientation during transport, storage and UV sterilization.

Once the rail cartridge 162 has been loaded with containers and inserted into the pockets 158 and 160, the tray 152 is environmentally sealed by heat sealing the plastic film lid 154 to the tray flange 156 in a distinct orientation. For illustrative purposes in FIG. 10, the film lid 154 is depicted halfway through the sealing process, with a portion of the lid lifted up to show the rail cartridge 162 nested within the tray 152. The film lid 154 is positioned on the flange 156 such that there is no "overhang" of the film lid material over the edge of the tray flange around the perimeter of the tray. In an exemplary embodiment, the plastic film lid 154 is constructed to have dimensions which allow the film lid to be positioned on the tray flange such that the film lid edge is inset from the tray flange edge around the entire flange periphery. In addition, the film lid heat seal is applied to extend beyond the edge of the film lid 154, to assure that no portion of the film lid edge left unsealed would create a loose edge "flap". Film lid orientation, placement and the avoidance of loose edges is particularly important to the surface ultraviolet (UV) decontamination process performed on the carrier 150 when the carrier is introduced to the aseptic zone. Crevices, caused by loose film lid edges and/or flaps, may cause a local shadow, when exposed to UV radiation, which shadowing effect can defeat the UV decontamination process.

Once the film lid 154 has been heat sealed to the tray flange 156, the carrier 150 defines a hermetically sealed environment that functions to isolate its contents from external contamination. The carrier 150 is subsequently placed into a polybag overwrap (not shown), which acts as a "dust cover", and identified with an adhesive label which is placed on the over wrap.

Turning now to FIGS. 11a and 11b, the carrier rail cartridge 162 is depicted in its component form, ready for assembly, in FIG. 11a and in a fully assembled condition in FIG. 11b. The carrier rail cartridge 162 suitably comprises a plurality of injection molded, polystyrene T-beams 163a, b, c, d, e, and f, disposed at spaced-apart intervals so as to form longitudinally running slots 164a, b, c, and d therebetween. The polystyrene T-bars 163a–f are oriented with the legs of the T facing upwards (from the perspective of FIGS. 11a and 11b) and include press or snap-fit pins 165, adapted to mate with corresponding receptacles 166 on one or more spacer plates 167. The spacer plates 167, like the T-rails 163a–f, are constructed of an injection molded high impact polystyrene material such as FINA 825 manufactured and sold by Fina Oil and Chemical Company of Deerpark, Tex. The spacer plates 167 of the carrier rail cartridge 162 are provided to separate and maintain the T-rails 163a–f at pre-determined distances from one another. The spacer plates may include cutouts 168 arranged to provide hand holds so that the final carrier rail cartridge assembly may be easily grasped, lifted and moved. Alternatively, a thin, flexible plastic handle may be attached to span spacer plates 167, or some other well known means may be provided by which the carrier rail cartridge may be grasped and manipulated.

Figure 12A:
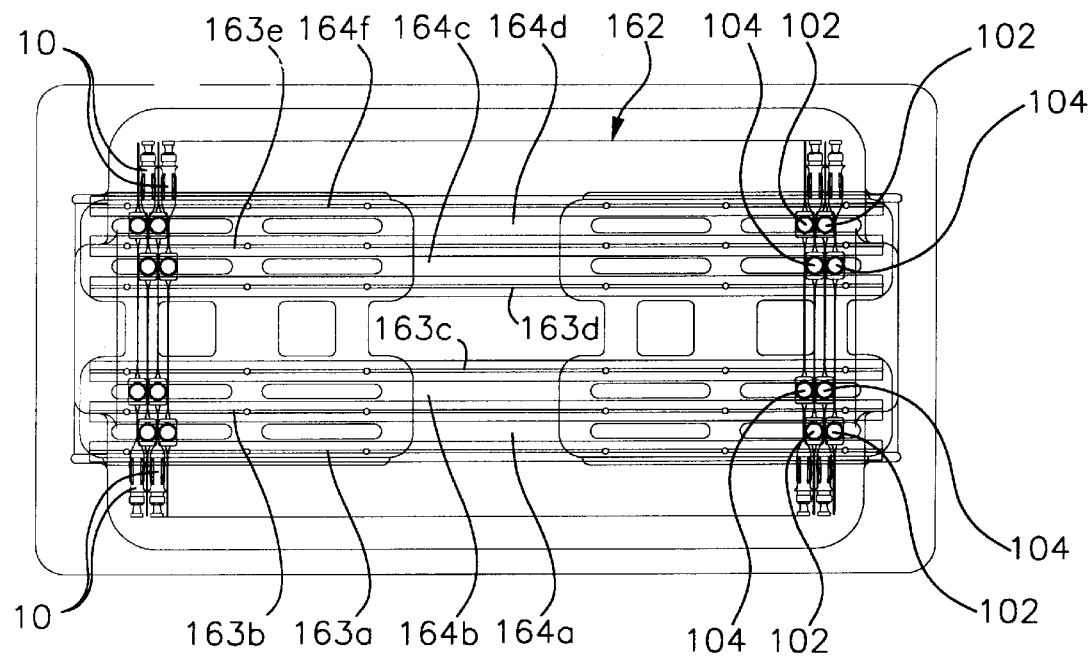
FIG. 12a is a semi-schematic plan view of the rail cartridge of FIGS. 11a and 11b depicting containers loaded onto the rails in accordance with the present invention.
Figure 12B:
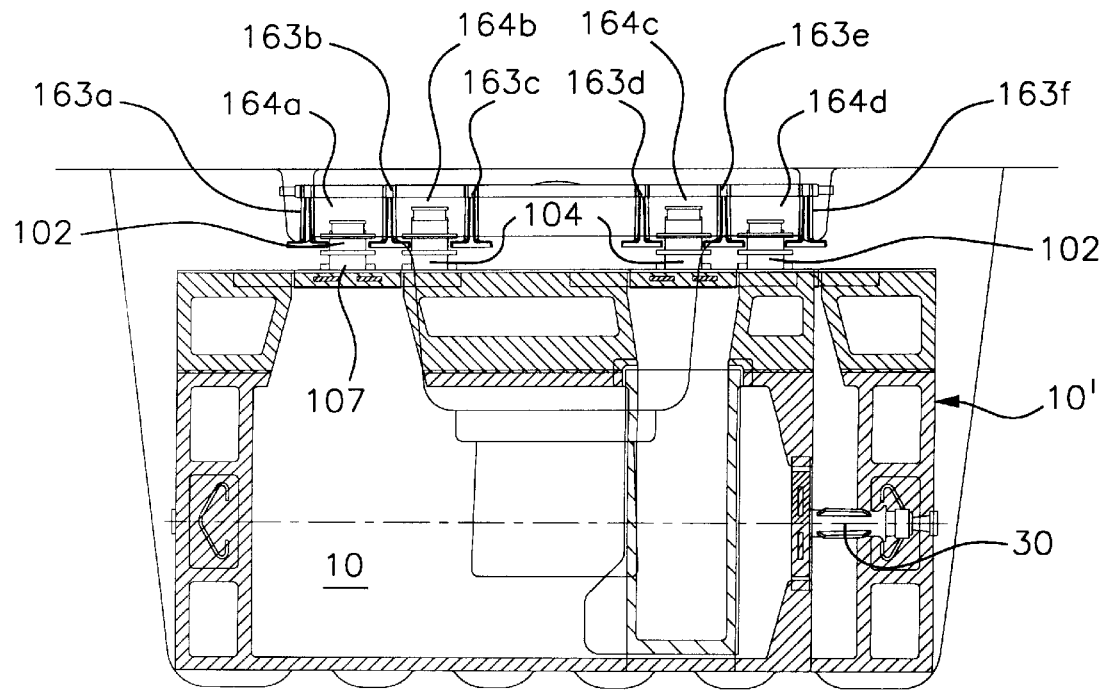
FIG. 12b is a semi-schematic front view of the loaded rail cartridge of FIG. 12a showing how containers are held within the rails by the sacrificial ports.

Once the carrier rail cartridge has been assembled, fabricated containers may be loaded onto the cartridge in accordance with the invention, in a manner depicted in FIGS. 12a and 12b. In FIG. 12a, which is a plan view of a loaded carrier rail cartridge, finished containers 10, such as those depicted in FIG. 8, are loaded onto the carrier rail cartridge 162 by inserting their sacrificial ports (102, 104) into the slots 164a–d formed between the cartridge's T-rails 163a–f, in the manner depicted in FIG. 12b. The flange edges of the T-rails 163a–f are spaced-apart a sufficient distance (about 13.0 mm) such that the central filling barrel 107 of each sacrificial port is able to be accommodated therebetween, and are adapted to engage the sacrificial ports between the port's circumferential flanges (103 and 105 of FIG. 8) such that each container 10 is grasped by the T-rail flanges beneath its uppermost circumferential sacrificial port flange 105.

In the exemplary embodiment of the carrier rail cartridge depicted in FIGS. 12a and 12b, four slots 164a, b, c, and d are provided for receiving containers, with the containers loaded onto the rail cartridge 162 in alternating left and right orientations. The sacrificial ports 102 and 104 of each container are inserted into two of the slots 164a–f. As depicted in FIG. 12b, a first container 10' is loaded into the second and fourth slots (164b and 164d) and is oriented in a first horizontal direction, such that its hanger end is oriented to the right, (from the perspective of FIG. 12b), and its set port is oriented to the left. The second container 10 (the front container from the perspective of FIG. 12b) is loaded onto the rail cartridge 162 with its sacrificial ports 102 and 104 inserted into the first and third cartridge slots 164a and 164c. The second container 10 is loaded in a second horizontal direction with its set port 30 oriented 180° with respect to the first container. In the example of FIG. 12b, the set port 30 of the first container 10 is on the right hand side when viewed from the perspective of FIG. 12b. Further containers are loaded onto the carrier rail cartridge 162 in like fashion, with the container's horizontal orientation alternating left and right; the sacrificial ports of the left oriented containers inserted into the second and fourth slots, the set ports of the right oriented containers loaded into the first and third slots, as described above, until the carrier rail cartridge 162 is completely filled.

Returning now to FIG. 12a, it will be understood that the particular design of the flanges of the sacrificial ports 102 and 104, in cooperation with the carrier rail cartridge 162, functions to maximize the packing density of containers within the container tray 152. As can be seen in FIG. 12a, the sacrificial port flanges protrude only along the length direction of each container, and not along its width or thickness dimension. Accordingly, as the carrier rail cartridge is filled, the thickness of any one particular container is defined by the width of its sacrificial port barrel (approximately 12.0 mm). As succeeding containers are loaded onto the carrier rail cartridge, only the filling barrels of the sacrificial ports of alternating containers come into contact with one another. Alternating the horizontal orientation of consecutive containers, as well as alternating their slot offset position, also assists in enhancing the packing density of containers in a fully loaded rail cartridge. As can be seen from FIG. 12a, providing a second set of slots allows the container packing density to be substantially doubled, in contrast to a carrier rail cartridge system with only a single pair of slots.

It will be evident to one having skill in the art that containers are loaded onto the carrier rail cartridge and held therein in a systematically aligned orientation such that each alternating container is 180° opposed to the previous container as well as being laterally offset from the previous container by the slot spacing of the cartridge. It will be understood that this alternating container orientation maximizes the packing density of containers along the length of the cartridge as well as defining specific orientations and locations of a multiplicity of containers with respect to the cartridge rails, for easy adaptation of the cartridge assembly to an automated loading and unloading system. The carrier rail cartridge and container loading sequence allows the cartridge to be temporarily "docked" or mounted to pick-and-place robotic machinery. Further, the cutouts (or thumb holes) 168 in spacing plates 167, allow an operator to easily insert and remove a filly loaded cartridge from the carrier tray without unduly tilting the cartridge, thus minimizing the possibility of containers falling off the rail.

Following loading, the carrier rail cartridge is placed within the tray 152 with the ends of the T-rails 163a–f nested in the pockets 158 and 160 formed in the ends of the tray. Pockets 158 and 160 support the carrier rail cartridge 162 within the interior volume of the tray and provide additional lateral support which prevents the cartridge from shifting during shipping, sterilization and storage.

The sealed carrier, including the empty containers within, is wrapped in a poly bag and transported to a radiation sterilization facility where it and its contents are rendered sterile by an E-beam sterilization procedure, for example.

Container Filling Process

After the foregoing carrier loading and E-beam sterilization procedure is completed, the sterilized medical containers are transported to an aseptic filling facility, and the containers are aseptically filled in accordance with one embodiment of the invention as is described with reference to an exemplary process flow-chart depicted in FIG. 13 and an exemplary filling apparatus depicted in semi-schematic, plan view in FIG. 14.

Primary bag filling will take advantage of manufacturing technology developed in connection with integrated circuit fabrication that is becoming more common in the medical industry. This technology generally involves a move away from conventional container filling in class 100 aseptic environments, to container filling within an "isolator" unit in which the environment is sterile. The main distinction between class 100 aseptic environments and "isolators" is the separation of the worker from the environment. An isolator is in essence, a "mini environment" which encloses the immediate machinery and container filling operation within a controlled space. The worker is separated from this space and interfaces with the materials therein through glove ports and/or "half suits". By separating the worker from the environment, it is possible to create and maintain a small, sterile environment, since the worker is typically the major source of biological contaminates.

The isolator is initially sterilized with a sterilant such as vaporized hydrogen peroxide (VHP). Inside the isolator, the ambient atmosphere is maintained in the sterile condition by supplying it with HEPA and ULPA filtered air. The ambient atmosphere within the isolator is also maintained at a higher pressure than the ambient atmosphere surrounding the isolator. Positive air pressure ensures that air flow is always from the inside of the isolator to the outside.

All components or sub-assemblies that will enter the isolator are either pre-sterilized or sterilized just prior to placing them in the isolator so that the sterile environment is maintained. Components are typically placed in isolators via doors or through entry/exit ports commonly referred to as RTPs (rapid transfer ports). RTPs are designed to mechanically interlock in a manner such that sterility is not compromised. Containers which carry sterile components to the isolator are sterile on the inside and include an RTP integral to the container.

Figure 13:
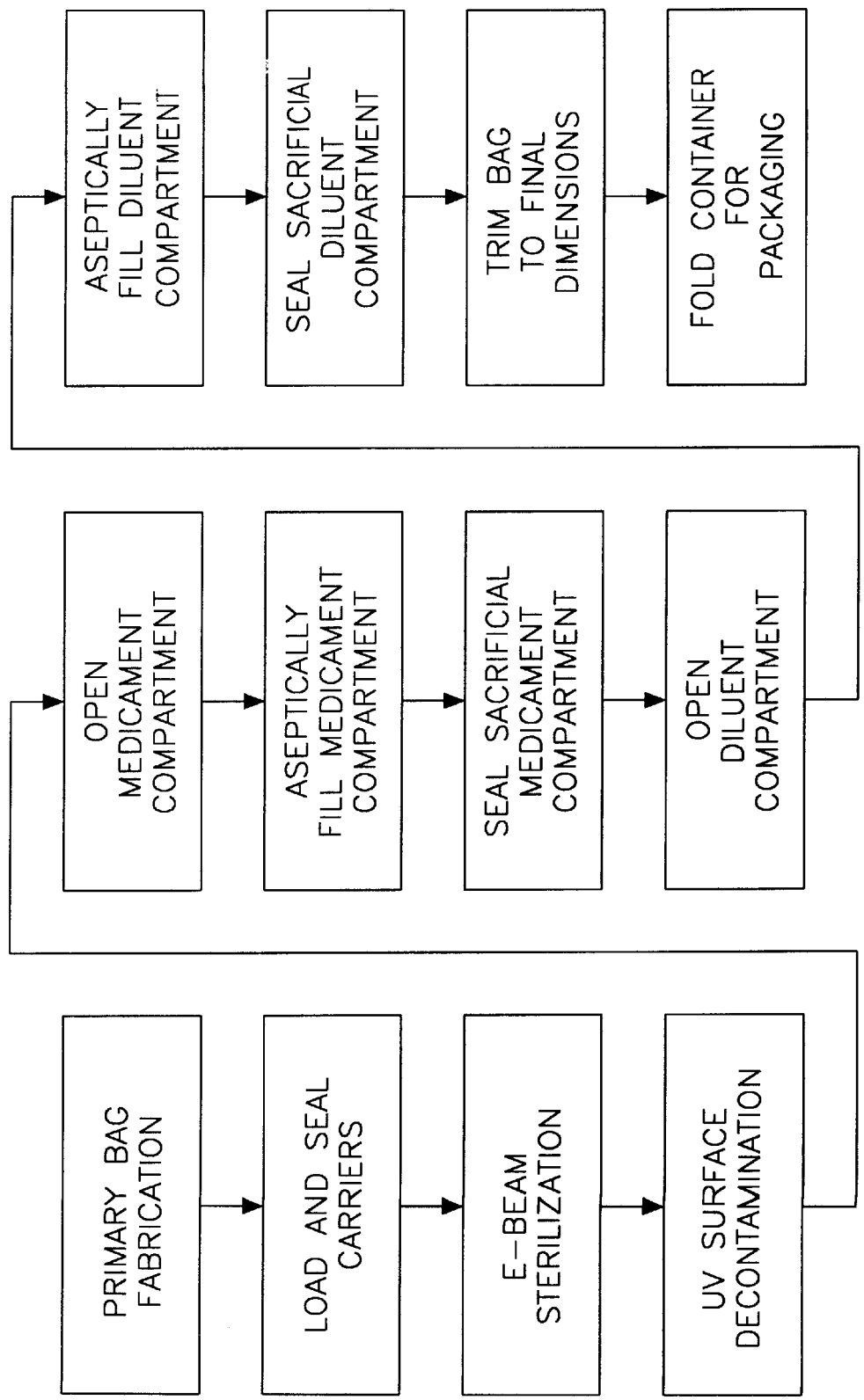
FIG. 13 is a flow chart of the sterilization and aseptic filling process for one embodiment of a container in accordance with one embodiment of the present invention.
Figure 14:
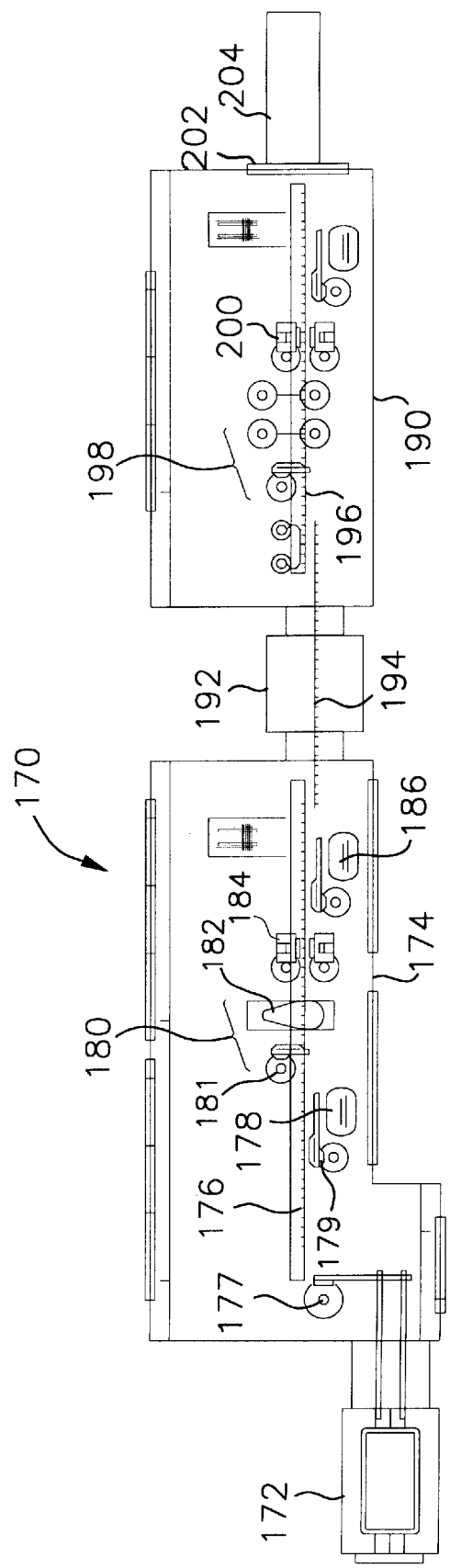
FIG. 14 is a semi-schematic plan view of an embodiment of a modular container filling apparatus showing the progressive process stations in accordance with practice of the present invention.

Turning now to FIGS. 13 and 14, and having particular reference to FIG. 13, before the carriers are introduced into the filling line, the poly bag over wrap is removed from each loaded carrier under unidirectional HEPA filtered air in order to maintain a low level of particulate matter and bio burden on the outside surface of the carriers. Following the poly bag over wrap removal, each carrier is individually tested for hermetic integrity by pressure decay, again under unidirectional HEPA filtered air.

Turning now to FIG. 14, in combination with FIG. 13, assuming that each carrier's integrity has been maintained throughout transport and E-beam sterilization, the carrier is introduced into the filling line, generally indicated at 170, by being passed through a UV decontamination tunnel 172, within which the outside of the carrier is surface decontaminated by UV radiation prior to the containers being removed from the carrier for filling. The carrier is inserted into the entry end of the UV tunnel 172, wherein UV emitting lights surround the carrier and irradiate the entire exterior surface to control potential contaminates from being introduced into subsequent isolators of the filling line.

After the UV cycle is complete, the carrier is transferred, through a chamber transfer door, into a carrier entry chamber (not shown) in which the carrier film lid is opened and the rail cartridge, including the containers, is removed from the carrier. Containers are removed from the rails of the cartridge and placed on tracks from which they are indexed onto a pick-and-place swing-arm 177 for transfer into a first filling isolator 174, which in the exemplary embodiment of the invention is a controlled environment for filling containers with, for example, powdered medicaments. Although the foregoing transfers may be accomplished by the use of automated equipment, transfer is typically performed manually, by reaching into the carrier entry station through "glove ports" or alternatively through the arms of a "half-suit" and manipulating the carrier, lid and cartridge. At this time, the empty rail cartridge and carrier are transferred back into the UV chamber and the transfer door is closed prior to removal of the cartridge and carrier from the UV chamber 172.

Figure 15A:
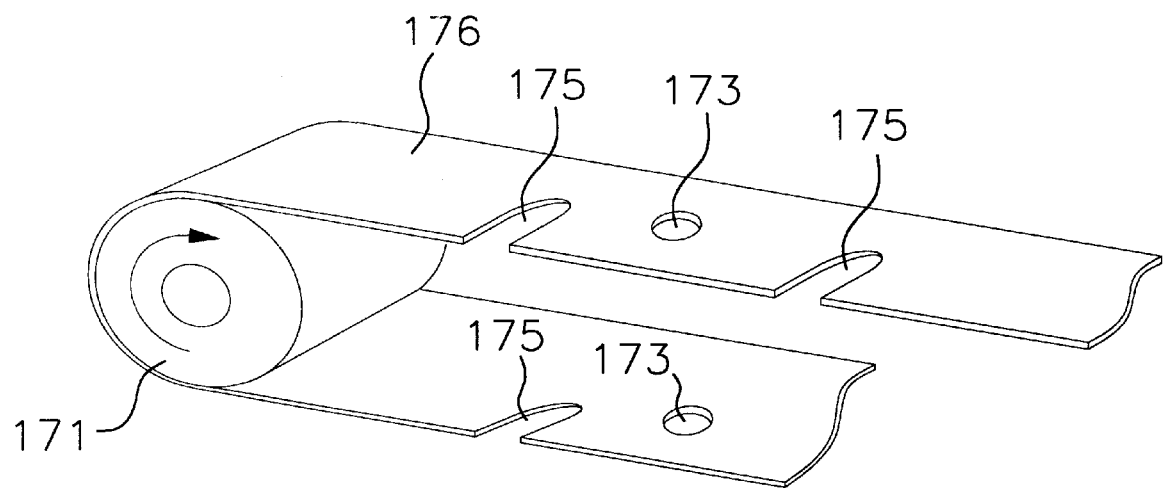
FIG. 15a is a semi-schematic pictorial cut-away view of a portion of a container transport band in accordance with practice of the present invention.

The pick-and-place arm 177 rotates a container to a position for loading onto a continuous-band transport mechanism, by means of which containers are introduced into the powder fill isolator 174 and subsequently indexed through the operational steps of the powder filling process. A portion of the continuous-band transport mechanism 176 is depicted in FIG. 15*a* and generally comprises a flat band of a suitable flexible material, such as metal or plastic and which forms a loop around the outside peripheral surface of a drive roller 171. The drive roller 171 is connected to a drive motor, such as a conventional D.C. motor or a stepper motor, which causes the transport band 176 to be indexed, in pre-determined, spaced-apart stages through the isolator. The transport band 176 includes a series of spaced-apart slots 175 which are cut into the band material in a direction orthogonal to the band's direction of travel. Each of the slots 175 has a width of about 12.4 mm, so as to accommodate the filling barrel of a container's sacrificial ports. Accordingly, the slots 175 are configured with a width sufficient to receive the filling barrel but are also sufficiently narrow to engage the underside surface of a sacrificial ports bottom most flange (103 of FIG. 8*a*).

A hole 173 is disposed intermediate a pair of slots, and is provided all the way through the material of the transport band 176. Each hole 173 has a diameter of about 11.0 mm and functions to provide a convenient receptacle for receiving a sacrificial port cap (109 of FIG. 8*a*) when a cap has been removed from a sacrificial port for filling. Although the hole 173 is depicted in the exemplary embodiment of FIG. 15*a* as positioned equidistant between two slots 175, it will be evident that the location of the hole (or cap receptacle) 173 may be provided anywhere in proximity to the slots 175. If robotic pick-and-place equipment, for example, is used to remove the caps from the sacrificial ports, all that is required is that each cap receptacle 173 have a specific relationship to the slots 175 such that the position of the cap receptacle 173 may be programmed into the robotic equipment.

Returning now to FIG. 14, containers may be removed from the rail cartridge and loaded onto the transport band 176 by hand; an operator reaching into the isolator by means of a half-suit or flexible arm coverings, accessed through gasketed ports or, alternatively, containers can be loaded onto the transport band 176 by an automated pick-and-place swing-arm 177 which grasps each container and rotates it through approximately 90° to mate the sacrificial port flanges with the transport band recesses.

Initially, the transport band 176 indexes each container to a tare weight balance 178 (shown in FIG. 14) at which the tare weight of each container is determined in order to provide a reference empty weight against which to correlate subsequent checkweighs. The empty container may be removed from the transport band 176 and placed on the tare weight balance either by hand or by means of an automated pick-and-place robotic arm 179. Next, the container is reintroduced to the transport band and indexed to an aseptic, rotary, in-line powder filler 180.

At the powder filler 180, a robotic arm 181 swings through an arc to engage the cap on the sacrificial port of the medicament compartment (104 of FIG. 8). The cap is removed by grasping it by its removal flange (as described in connection with FIG. 8*a*) and exerting a vertically upward force. After removal, the medicament compartment sacrificial port cap is deposited in the cap receptacle (173 of FIG. 15*a*) located between the sacrificial port slots on the transport band. The medicament compartment sacrificial port cap is now in a known location with respect to the medicament compartment sacrificial port, such that robotic machinery may now easily retrieve the cap for reinsertion into the medicament compartment sacrificial port as will be described further below. Following cap removal, the medicament compartment is opened (de-blocked) with a jet of 0.2 micron filtered nitrogen or air, introduced through the filling barrel of the medicament compartment sacrificial port.

Figure 15B:
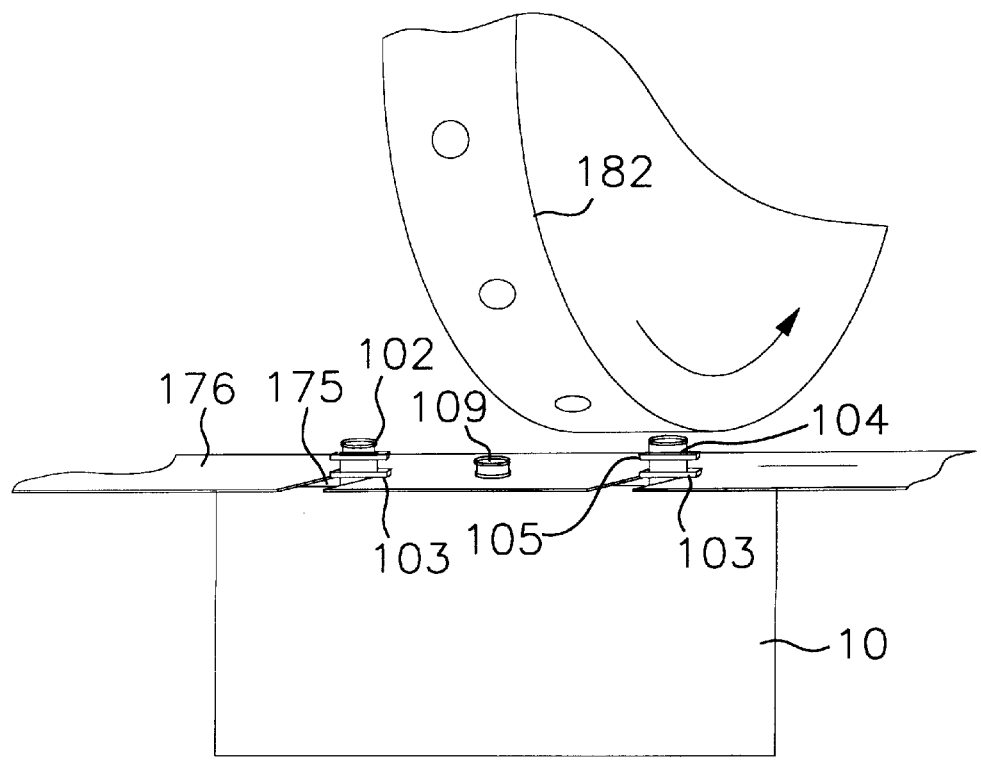
FIG. 15b is a semi-schematic partial perspective view of the arrangement of a powder filling wheel and transport band showing the direction of travel of containers beneath the filling wheel.

Turning now to FIG. 15*b*, the transport band next indexes the container to a position where the medicament compartment sacrificial port is beneath a conventional, generally circular dosing wheel 182 which automatically dispenses a pre-determined amount of powdered medicament into the medicament compartment though the open port. The dosing wheel 182 is oriented in a direction orthogonal to the direction of travel of the transport band 176 and the containers 10 hung therefrom. Accordingly, the reason for the medicament compartment port's being taller than the diluent compartment's port now becomes apparent. In order that the entire powder charge contained in the dosing wheel is introduced into the medicament compartment without undue spillage, the medicament compartment's port is sized to place its open throat in proximity to the dosing wheel at a distance of approximately 1.0 millimeters. In order for the diluent compartment's port, including the still affixed cap, to clear the underside of the dosing wheel after dosing is completed and as the container is indexed to the next station, the total height of the diluent compartment port and cap combination must be no greater than the height of the medicament compartment port with the cap removed, i.e., no greater than the space between the transport band 176 and the dosing wheel 182.

An alternative configuration can be devised with regard to the orientation of the containers and the dosing wheel. For example, rather than traveling in-line, along their long axis, the containers could be introduced to the dosing wheel face-on, such that only the medicament compartment sacrificial port passes beneath the bottom of the arc of the dosing wheel. This particular orientation would allow the diluent port to avoid the narrow space between the transport band and the bottom of the dosing wheel arc and thus preclude the necessity of providing sacrificial ports of separate heights.

Returning now to FIGS. 13 and 14, following powder fill, 0.2 micron filtered nitrogen gas or air is introduced into the medicament compartment's head space and the transport band 176 indexes the compartment to a heat seal station 184. Although both 0.2 micron filtered nitrogen gas or air are within the contemplation of the present invention, it will be understood that the choice between these two gasses, or other filter sterilized gasses (inert or otherwise) will depend upon the sensitivities of the particular drugs introduced into the medicament compartment. Specifically, if a drug is extremely sensitive to oxidation, the medicament compartment's head space will preferably be filled with filter sterilized nitrogen, or a similar inert gas. At the heat seal station 184 opposed heat seal heads are brought together to either side of the container, to thereby close-off the channel (112*b* of FIG. 8) between the sacrificial port and the medicament compartment. The heat seal, thus formed, effectively continues permanent seals between the oversized edge seals 110*e* and 110*f* depicted in FIG. 8, thus sealing the medicament compartment.

Next the cap is reinserted into the medicament compartment sacrificial port and, the powder filled container is indexed to a gross weight balance 186 where its gross weight is taken to verify that the proper amount of powdered drug has been dispensed into each container. The gross weight, as determined at station 186 is correlated to the weight of the empty container as determined at the tare weight station 178. If the gross weight balance 186 determines that an improper amount of powdered drug has been introduced into the container's medicament compartment, the container is rejected and transferred to a reject rail cartridge for subsequent removal from the powder fill isolator 174. If the checkweigher determines that the amount of powdered drug in the medicament compartment is correct, the container is deemed to have been correctly filled and is indexed to the next station, or stations, if additional processing is desired.

In accordance with practice of principles of the invention, additional compartments of a container may be filled by additional medicaments or by diluents (follow-on filling) in a subsequent isolator unit, or multiple follow-on isolator units. Although the first filling step was described in connection with the introduction of a powdered drug into the medicament compartment, it will be understood that this was performed in the context of a multiple compartment medical container having separate compartments for a powdered medicament and a liquid diluent. However, it will be evident that a single compartment medical container can be filled in accordance with the present invention, by either a powdered drug, in the manner described above, or a liquid diluent or drug, in a manner to be described below.

Having particular reference to FIG. 14, the partially filled multiple compartment container of the exemplary embodiment of the invention, is now introduced to a second, liquid fill isolator unit 190 for aseptic filling with a diluent.

In particular, at the completion of the powder fill process, and as indicated in the exemplary process flow chart of FIG. 13, the partially filled container is moved from the powder fill isolator 174 to the liquid fill isolator 190 through a transfer tunnel 192 which is connected between the two isolator units. Following the above-described powder filling procedure, the container is removed from the transport band 176 of the powder fill isolator 174, and placed on a transfer band 194 which passes through the transfer tunnel 192 and which links the two isolator units. It will be understood by those having skill in the art that the transfer tunnel 192 and transfer band 194, in combination, provide an essential feature which promotes the modular nature of the isolator based filling process of the present invention. Indeed, it may be seen that a multiplicity of isolators may be linked together by transfer tunnels so as to add additional filling steps, with perhaps a multiplicity of ingredients, to the process. The modular nature of the container construction process, by which single or multiple compartment containers may be manufactured, interfaces easily with the modular nature of the filling process. As many fill isolators as are necessary to fill the desired number of compartments, may be easily linked together with transfer tunnels to thereby realize a manufacturing and filling line of complete flexibility.

Returning now to the filling process and apparatus of FIGS. 13 and 14, the partially filled containers are introduced into the liquid fill isolator 190 through transfer tunnel 192 and are again placed on a continuous-loop transport band 196 which indexes the container through the steps of the liquid filling process.

As was the case with the previously described powder filling process, each container is indexed to a fill station 198 at which a robotic arm moves through an arc to grasp and remove the cap from the diluent compartment's sacrificial port and place it in a receptacle on the transport band. The diluent compartment is next de-blocked with a jet of 0.2 micron filtered nitrogen or air and advanced to place the diluent compartment sacrificial port beneath the dispensing nozzle of a diluent filling machine. A pre-determined amount of diluent, such as normal saline or 5% Dextrose Injection diluent is dispensed into the container through the sacrificial port. The diluent has typically been pre-mixed under qualified procedures in a separate mixing area and piped to the filling machine through 0.2 micron filters. It will be understood by those having skill in the art that diluent may be introduced to the container in a single dispensing step or, alternatively a dual dispensing step or multiple dispensing step procedure may be used in order to more accurately control the dose and minimize turbulence.

Following the diluent dispensing step the container is indexed to a diluent compartment heat seal station 200, where the diluent compartment head space is first adjusted with 0.2 micron filtered nitrogen or air. The heat seal station 200 comprises a heat seal platen opposed to a backing plate, which next are closed over the container so as to seal off the channel (112*a* of FIG. 8) between the diluent compartment and its sacrificial port. In effect, the diluent compartment heat seal continues the permanent peripheral seal between regions 110*d* and 110*e* of FIG. 8, thus completely sealing off the now completed container from the sacrificial strip.

The filled container now exits the liquid fill isolator 190 by an exit tunnel pass-through 202 and exit conveyor 204. The container is rinsed and dried to remove any residual diluent and/or medicament from its exterior surface and is trimmed to its final dimensions by removing the oversized edge portion of the container which includes the sacrificial ports. As an optional part of the trimming process, the peripheral seal along the side of the container which is to be trimmed away may be reinforced thus ensuring the seal of the medicament and diluent compartments on all sides of the container. Container fabrication and filling is now complete and the finished and filled container is folded-over along the seal between the medicament and diluent compartments, over-wrapped, and packed into shipping containers.

The production process for fabrication and filling of the container thus contemplates only a single sterilization procedure following the fabrication of the primary container. According to practice of principles of the invention, the construction of the container and the use of sacrificial ports communicating with the diluent and medicament compartments, allows the diluent and medicament compartments to be subsequently aseptically filled, and sealed without the need for any further sterilization procedures. Indeed, since the container of the present invention is not able to be terminally sterilized by steam, because of the high moisture sensitivity of powder medicaments and the moisture barrier properties of the medicament compartment cover, the aseptic filling methods, described above, are a necessary adjunct to the manufacture of a sterile final product. Fabrication and filling of the container in accordance with practice of the invention thus allows the container to be fabricated from materials, including high-barrier property laminates which are highly resistant to the effects of conventional steam sterilization. Once the requirement for down-stream sterilization is removed, medical containers may be constructed to include such high-barrier laminates, thus providing medical containers which are particularly suited for long term storage, and which may be efficiently fabricated with a low manufacturing cost.

In addition, it will be understood by those having skill in the art that the construction and use of the sacrificial ports communicating with the diluent and medicament compartments provides a means to index, retain, position and manipulate the container throughout the filling process. The size of the sacrificial port openings adapts the container to be compatible with conventional drug vial filling equipment technology.

The sacrificial ports are designed with flanges so that the container is able to be hung on an indexing mechanism, and two flanges are provided on each port so that the container can be "handed off" by robotic pick-and-place equipment to off-line checkweighing stations or be transferred between isolators. In addition, it will be seen that using sacrificial ports, in connection with medical container fabrication and filling processes, ideally promotes modularity in the fabrication and filling sequence.

Use of the Container

Figure 16:
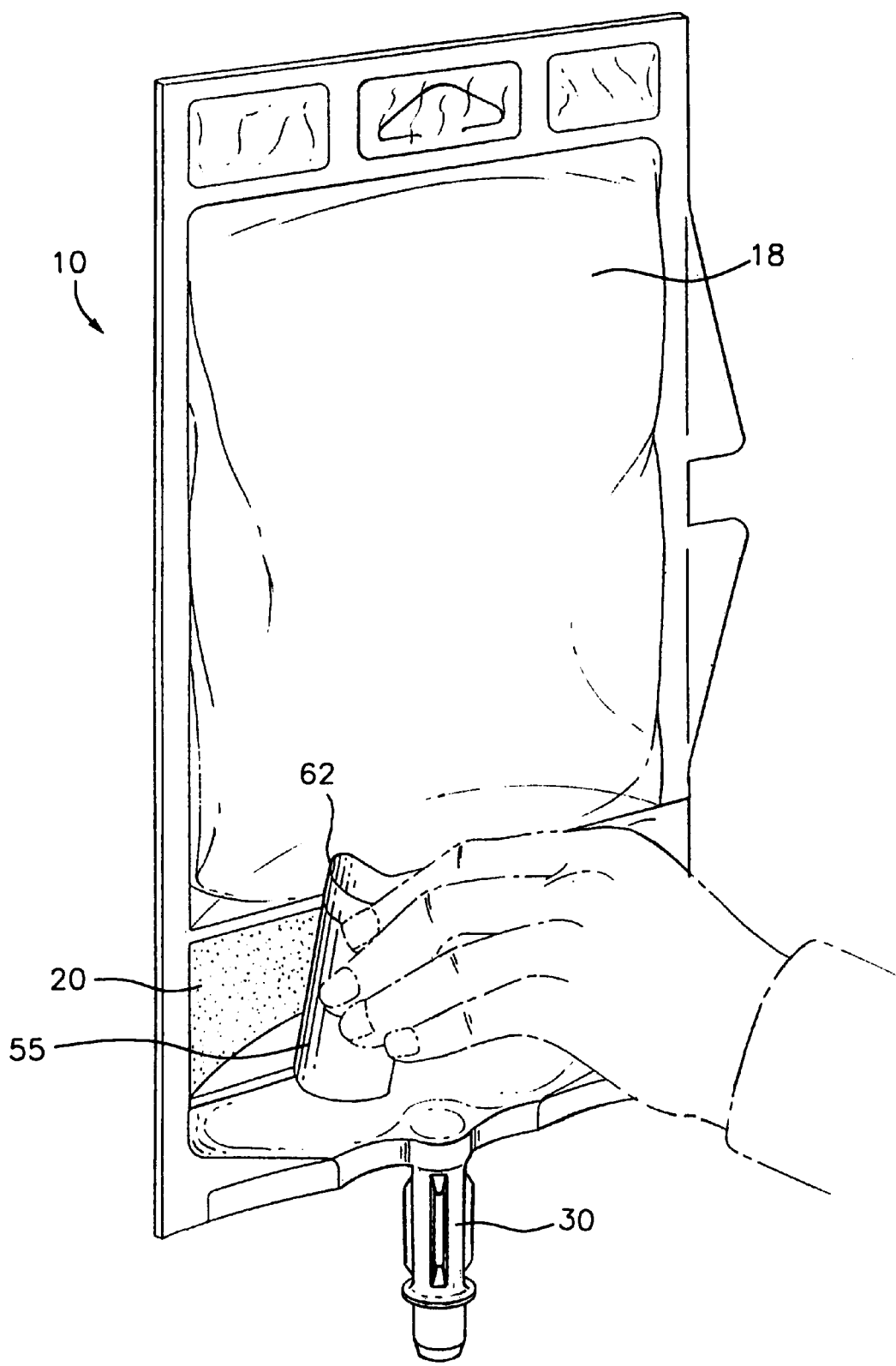
FIG. 16 is a semi-schematic pictorial view showing a peelable medicament compartment cover being removed for inspection of the medicament prior to mixing and use.
Figure 17:
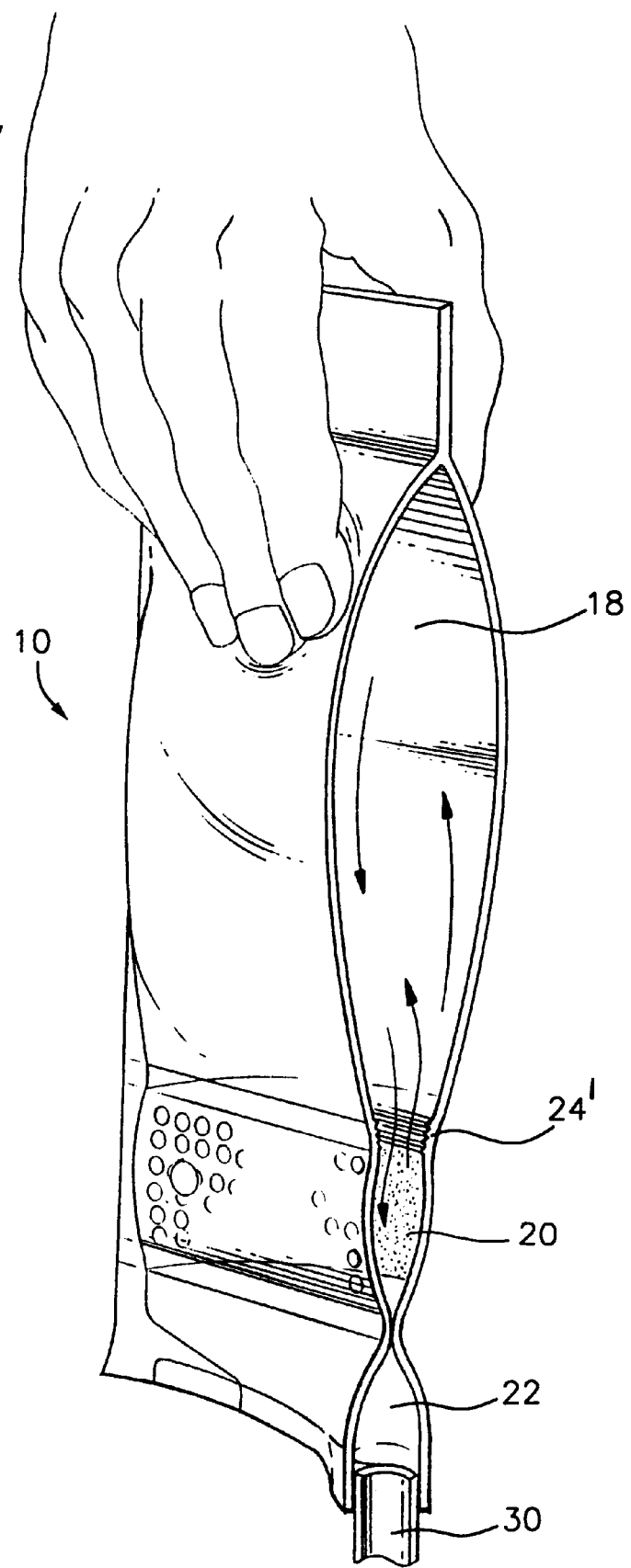
FIG. 17 is a semi-schematic pictorial cut away view demonstrating the manipulation of the container to separate the first peelable seal to mix the diluent and medicament.

Use of the completed containers is substantially independent of the production technique employed. The triple compartmented container 10 and mixing system will be received by health care personnel, typically a hospital's pharmacy department, in the completed configuration shown in FIGS. 1 and 2. Referring now to FIG. 16, in preparing to use the container, the medicament may be inspected by grasping the tab 62 on the aluminum foil-containing protective layer 55 and peeling the protective layer from the container to enable visual inspection of the intermediate compartment 20 containing the powdered medicament. If the medicament appears dry and in normal condition, the solution can be mixed as shown in FIG. 17 by manipulating the container to compress the front and rear sheets in the area of the upper diluent compartment 18. Mechanical pressure from the hydraulic forces created by manipulation of the container ruptures the peelable seal between the diluent and medicament compartments (shown in the ruptured condition as 24'). Further manipulation by shaking causes mixing of the liquid diluent and powdered medicament. Verification that complete mixing is obtained is made by visually observing the mixed solution through the clear, transparent front sheet. After mixing is complete, the peelable seal between the medicament compartment and the lower security compartment is broken as shown in FIG. 18 by again compressing the front and rear sheets of the container creating hydraulic pressure in the container to rupture the seal (shown in the ruptured condition as 26'). The mixed solution is then dispensed from the container through the outlet port 30 using a standard IV delivery device.

The arrangement of the container 10 precludes delivery of unmixed diluent through the outlet port 30. Further, the arrangement of the intermediate compartment 20 between the diluent compartment and the outlet port enhances the probability of complete mixing and delivery of the medicament to the patient. For containers including a liquid diluent and powdered medicament, rupture of the first peelable seal between the diluent compartment 18 and medicament compartment 20 is essentially assured prior to rupture of the second peelable seal between the medicament compartment 20 and the lower security compartment 22 since the hydraulic forces developed in the diluent by manipulating the container cannot be transmitted through the powder in the medicament compartment until the first seal has been ruptured and mixing of the diluent and powder has commenced. For those cases where a liquid medicament may be used, the relative size difference between the diluent compartment and the medicament compartment and the placement of the smaller medicament compartment intermediate the larger diluent compartment and the lower or security compartment assures development of hydraulic forces which will rupture the first seal between the diluent and medicament compartments before rupture of the second seal leading to the security compartment with only minimal care.

Figure 18:
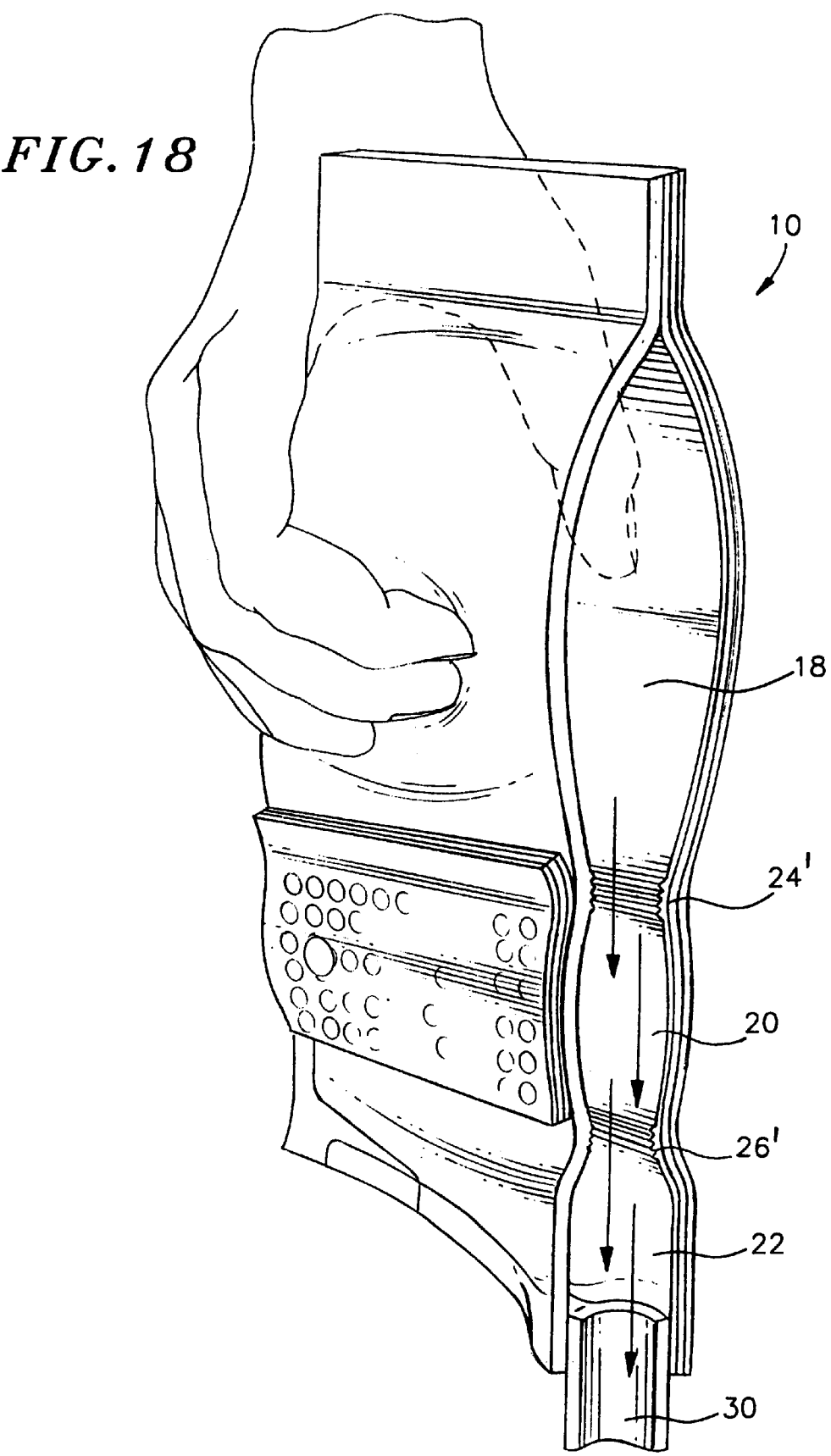
FIG. 18 is a semi-schematic pictorial cut away view demonstrating the manipulation of the container to separate the second peelable seal to dispense the medicament solution.

In the exemplary embodiments of the container, shown in FIGS. 16, 17, and 18, the peelable seals are depicted as having a conventional, rectangular, shape such as the seals described in U.S. Pat. No. 5,176,634 to Smith et al. the disclosure of which is expressly incorporated herein by reference. In accordance with practice of principles of the invention, the seals, although conventionally shaped, are formed in the manner described above to provide a uniform, predictable response to manipulation pressure and peel open at an applied force of about 4.0±1.0 psi. In an additional embodiment of the invention, curvalinear peelable seals are provided which function to peel open completely, along their lengths, under hydraulic pressure, and which are formed in substantially the same manner as the uniform peelable seals described above.

Figure 19:
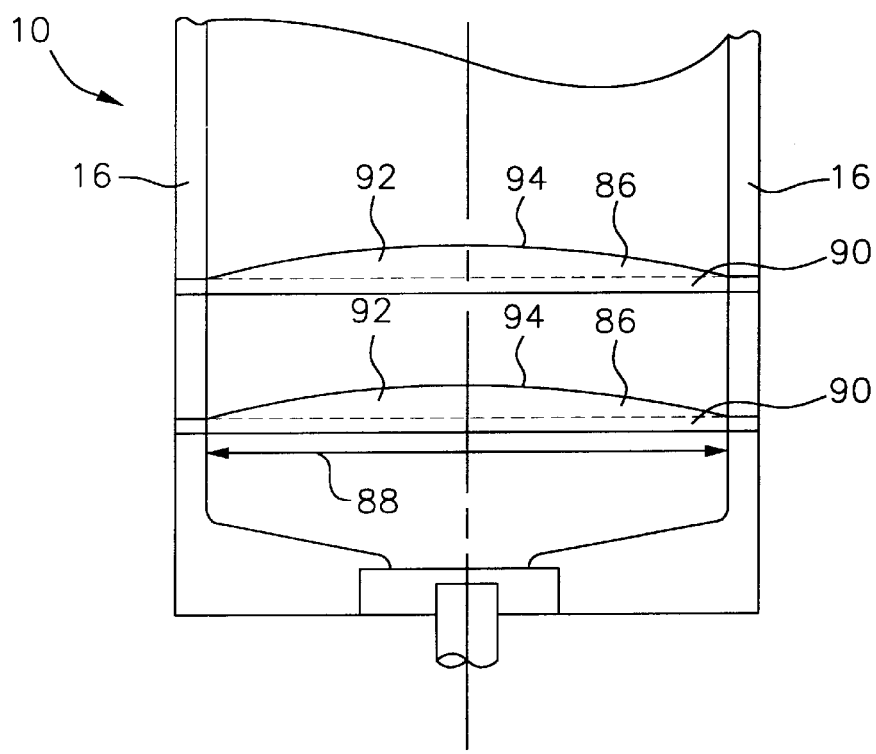
FIG. 19 is a semi-schematic partial front view of one exemplary embodiment of a medical container showing the construction and arrangement of the curvalinear seals.

Turn now to FIG. 19, which depicts a semi-schematic view of an exemplary embodiment of a curvalinear peelable seal 86 provided in accordance with practice of the invention. The curvalinear seal shape is provided in order to resolve two conflicting performance requirements imposed on peelable, or frangible, seals used in connection with a binary medical container. The first, performance requirement for a peelable, or frangible, seal is that it provide a relatively strong resistance to the force required by a product user to break or peel the seal, in order to avoid inadvertent rupture of the seal during normal handling. The second performance requirement is that the seal peel substantially completely apart during user activation, thus avoiding any subsequent restriction of the flow path between communicating chambers. It has been noted that with conventional, straight, peelable seals, there is a possibility for the seal, whether peelable or frangible, to incompletely peel apart during activation. This may allow significant amounts of either liquid diluent or mixed medication to remain trapped against the unopened seal line portions. In addition, it has been noted that for conventional, straight, peelable seals, that when the force required for user activation increases, so too does the probability of incomplete seal opening.

Operational use of a binary medical container requires that the peelable seals survive various impacts during the products' lifetime. The majority of these impacts will tend to occur while the product is folded-over along a seal line, with the peelable seals being thus well protected. However, significant impact events may occur after the product has been unfolded and, during this period, the peelable seals are susceptible to unanticipated activation with subsequent product activation. In order to reduce the risk of unanticipated activation, an effective binary medical container should be constructed with peelable seals strong enough to resist most inadvertent impacts, yet completely yield to the pressures of intentional manipulation.

Accordingly, the curvalinear peelable seal 86 resolves the two conflicting performance requirements by having a shape which mirrors the shape made by a conventional, straight, peelable seal as it begins to peel apart. As is described above in connection with FIGS. 1 and 2, and as shown in FIG. 19, the peelable seals span the container horizontally, and have a length 88 sufficient to connect between the permanent seals 16 on the sides of the bag, thus dividing the container into compartments. Each seal 86 comprises a first, generally rectangular, portion 90 which defines the minimum width of the peelable seal 86 at its intersection with the permanent seals 16 at the sides of the container. The dimension of the rectangular portion 90 in the height direction (the small dimension), is approximately 1/10 to 1/4 inch, and preferably 1/8 inch (0.125"). This rectangular portion 90 is thus shaped like a conventional rectangular (straight) seal. The peelable seal 86 further includes a second, curvalinear, portion 92 which comprises an arcuate section surmounting the rectangular portion 90, with the chord of the section coextensive with an edge of the rectangular portion, and with the arc of the section oriented to project into the compartment which will provide the source of the seals' opening pressure. The arc's convex edge 94 is generally radial and has a maximum depth of cord which is at least approximately one half of the width of the rectangular portion 90 of the seal 86. The specific shape, radius of curvature, and depth of cord of the curvalinear section 92 will, of course, vary with the length of the seal, and the particular application to which the binary container is put, including the anticipated strength of any inadvertent impacts. However, specific seal shapes may be suitably calculated, by one having skill in the art, using beam theory and suitably determining the desired opening pressure for the seal.

Figure 20:
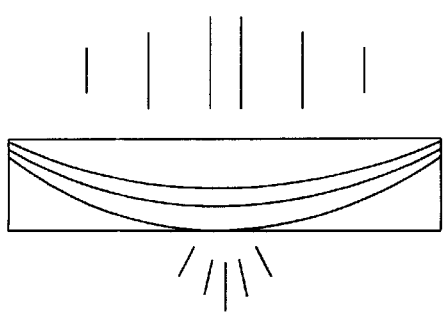
FIG. 20 is a semi-schematic front view of a conventional peelable se al showing, in phantom, the progressive phases of incomplete rupture of the seal.

In operation, the convex leading edge 94 of the peelable seal 86 presents a compound resistance characteristic to the hydraulic pressure of diluent, or mixed medication, when a respective compartment is squeezed. As depicted in FIG. 20, the peel characteristics of conventional, peelable seals exhibit a curved peel front, when the seal is examined after having been only partially peeled-open. This curved peel front indicates that the hydraulic pressure, forcing the seal open, is greatest in approximately the center of the seal, and decreases uniformly, but in accord with a power law outwardly toward the edges of the seal. A partially peeled-open conventional seal would, thus, have a concave separation pattern, with the deepest portion of the concavity being approximately in the center of the seal. It may, therefore, be easily seen that conventional seals will tend to naturally open soonest in the central region of the seal, and tend to remain closed along the sides of the seal, particularly where the peelable seal contacts the permanent edge seal.

Figure 21:
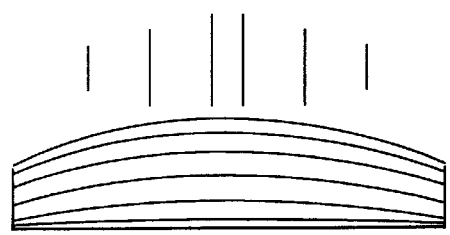
FIG. 21 is a semi-schematic front view of one exemplary embodiment of a curvalinear peelable seal provided in accordance with practice of the present invention showing, in phantom, the progressive phases of complete rupture of the seal.

In accordance with practice of principles of the invention, the curvalinear peelable seal 86 of FIG. 19 provides a convex edge 94 having a shape which is a mirror image of the concave peel characteristics of a conventional seal. As depicted in FIG. 21, the resistance characteristic of the curvalinear seal will match the curvalinear pressure gradient of diluent or mixed medication which is attempting to peel the seal open. The resistance characteristic of the curvalinear seal 86 is strongest at the center, where the pressure is greatest, and decreases in a non-linear fashion, in accordance with decreasing pressure, towards the edges of the seal. In this fashion, the seal is caused to peel open, uniformly, along its entire length.

Although the curvalinear peelable seal 86 has been described as providing a non-linear resistance characteristic to hydraulic pressure by having a curvalinear width, it will be evident to those having skill in the art that non-linear resistance characteristics may be provided by other means.

For example, a curvalinear resistance characteristic may be obtained in a rectangular shaped straight peelable seal by varying the temperature or pressure of a heat seal bar when forming the seal. The heat seal temperature may be made hottest at the center and made to non-linearly decrease towards the ends of the seal, thus providing a peelable seal which is strongest at the center, by virtue of the seal being more permanent. Alternatively, a curved sealing bar may be used to give the same effect, with the sealing bar being constructed to have a convex contact face which presses against the binary medical container during the peelable seal manufacturing process. While such a seal may exhibit a conventional linear shape, its central portion would be squeezed together much more tightly during the sealing process. Application of pressure would result in the central portion of the seal being the strongest, with the strength of the seal decreasing in a non-linear (curved) fashion towards the ends. All that is required, is that the peelable seal have a non-linear resistance characteristic which substantially matches the non-linear pressure characteristics of diluent, or mixed medication, when a respective compartment is squeezed.

Further, complete mixing of the diluent and medicament, and complete delivery of the mixed solution through the outlet port to a standard IV delivery device is enhanced by the non-linear peel characteristics of the seals of the present invention. As described above, the peelable seal's non-linear resistance to hydraulic pressure ensures that the seal opens substantially along its entire length and, thus, ensures that substantially all of the liquid diluent is able to enter the medicament compartment and mix with the drug contained therein. Following mixing, the non-linear peel characteristic of the second seal ensures that seal is peeled open substantially completely along its length allowing the mixed solution access to the outlet port and the IV delivery system.

Those skilled in the art will recognize that the primary discussion of embodiments comprising a liquid diluent and a single powdered medicament do not limit the scope of the invention. Use of liquid medicaments in the intermediate compartment or a plurality of compartments for powdered and liquid medicaments, to be mixed with the diluent, may be employed using the present invention. Multiple sacrificial ports and communication channels between the sacrificial ports and a respective compartment may easily be provided in accordance with practice of principles of the invention. Moreover, depending on the susceptibility of any of the components comprising the contents of the multiple compartments to moisture or free oxygen contamination, those compartments may be protected by additional applications of a clear, transparent $SiO_x$ containing, high-barrier laminate over the container front sheet in those compartment regions. Such high-barrier laminates may be provided with or without being combined with an aluminum foil containing high-barrier laminate peelable covering.

The above descriptions of exemplary embodiments of flexible, sterile containers are for illustrative purposes. Because of variations which will be apparent to those skilled in the art, the present invention is not intended to be limited to the particular embodiments described above. Such variations, and other modifications and alterations are included within the scope and intent of the invention as described in the following claims.

What is claimed is:

1. A method for forming a flexible container for combined storage and administration of medicaments and diluents for IV solutions, the method comprising the steps of:

providing a flexible, transparent front sheet;

providing a flexible, vapor impermeable rear sheet, the front and rear sheets sealed together at a common peripheral edge;

heating the front and rear sheets in a first localized area to fuse together the heated portions of the adjoining surfaces, thereby forming a first peelable seal extending between two sides of the common peripheral edge, the first peelable seal separably joining the front and rear sheets to thereby form a first compartment for containing a diluent;

heating the front and rear sheets in a second localized area to fuse together the heated portions of the adjoining surfaces, thereby forming a second peelable seal extending between the two sides of the common peripheral edge, the second peelable seal separably joining the front and rear sheets to thereby form an outlet compartment and a compartment for containing a medicament, the medicament compartment being between the outlet compartment and the diluent compartment;

providing first and second sacrificial ports interposed between the front and rear sheets and in communication with the diluent and medicament compartments, respectively;

filling the diluent compartment with a diluent solution through a respective sacrificial port;

filling the medicament compartment with a medicament through a respective sacrificial port; and completing the seal along the container's common peripheral edge and removing the sacrificial ports from the container, whereby container formation is completed without being subject to a sterilization step after the first compartment filling step.

2. The method according to claim 1 further comprising:
providing an isolator having a sterile environment, the ambient atmosphere within the isolator maintained in a sterile condition, wherein the diluent compartment and medicament compartment are aseptically filled with pre-sterilized diluent and pre-sterilized medicament in the sterile environment inside the isolator.

3. The method according to claim 1, wherein the first and second peelable seals are formed by maintaining the heat seal temperature in the range of from 245° F. to 265° F. while applying a pressure in the range of from about 230 psi to about 340 psi for a time in the range of from about 1.5 seconds to about 2.5 seconds.

4. The method according to claim 2 further comprising sterilizing said container before the initial compartment filling step.

5. The method according to claim 4, wherein said sterilization step comprises:
providing a transport carrier;
placing a multiplicity of containers into the transport carrier;
sealing the transport carrier against environmental contamination; and
sterilizing the sealed transport carrier and containers within by application of E-beam radiation.

6. The method of claim 5, wherein said sterilization step further comprises:
placing the E-beam sterilized sealed transport carrier into a UV decontamination chamber;
decontaminating the transport carrier by application of UV radiation; and
introducing the decontaminated transport carrier into the isolator without reexposing the carrier to ambient atmosphere.

7. The method according to claim 4, wherein the finished container is folded-over along the line of the first peelable seal between the medicament and diluent compartment.

8. A method for forming a flexible container for administration of IV solutions, the method comprising the steps of:
providing a flexible front sheet;
providing a flexible rear sheet, the front and rear sheets permanently sealed together around a portion of a common peripheral edge so as to define a volume enclosure therebetween, wherein at least one gap is present in the permanent seal;
providing at least one sacrificial port interposed between the front and rear sheets and in communication with the volume enclosure; and
heating the front and rear sheets in a first localized area to fuse together the heated portions of the adjoining surfaces, thereby forming extension seals in a portion of the container extending between two sides of the common peripheral edge and spaced-away from the at least one sacrificial port, the extension seals and the permanent seal gap defining a channel from said sacrificial port to said volume enclosure.

9. The method according to claim 8 further comprising the steps of:
filling the volume enclosure through said sacrificial port;
completing the permanent seal along the container's common peripheral edge so as to interrupt communication between the sacrificial port and the volume enclosure; and
removing the sacrificial port from the container, whereby container formation is completed without being subject to a sterilization step after the volume enclosure is filled.

10. The method according to claim 9 further comprising the step of sterilizing said container before the volume enclosure is filled.

11. The method according to claim 10, wherein said sterilization step is E-beam sterilization.

12. The method according to claim 11, further comprising:
providing an isolator having a sterile environment, the ambient atmosphere within the isolator maintained in a sterile condition, wherein the volume enclosure is aseptically filled with pre-sterilized material.

13. The method according to claim 12, wherein the pre-sterilized material is a pre-sterilized diluent liquid.

14. The method according to claim 12, wherein the pre-sterilized material is a pre-sterilized medicament powder.

15. The method according to claim 10, wherein said sterilization step further comprises:
providing a transport carrier, the transport carrier including a rail cartridge configured to receive and support a multiplicity of containers thereon, the rail cartridge engaging the containers by their respective sacrificial ports;
loading a multiplicity of containers onto the rail cartridge;
placing the loaded rail cartridge into the transport carrier;
sealing the transport carrier against environmental contamination; and
sterilizing the sealed transport carrier and containers within by application of E-beam radiation.

16. The method according to claim 15, wherein said sterilization step further comprises:
introducing the E-beam sterilized sealed transport carrier into a UV decontamination chamber;

decontaminating the transport carrier by application of UV radiation; and introducing the decontaminated transport carrier into an isolator having a sterile environment, without reexposing the carrier to ambient atmosphere.

17. A method for forming flexible container for combined storage and administration of IV solutions, the method comprising the steps of:

providing a flexible, transparent front sheet;

providing a flexible, vapor impermeable rear sheet;

heating the front and rear sheets in a first localized area to fuse together the heated portions of the adjoining surfaces, thereby forming a permanent seal around a portion of a common peripheral edge of said front and rear sheets, the permanent seal having at least one gap therein providing a channel between said front and rear sheets; and providing at least one sacrificial port interposed between the front and rear sheets and in communication with the channel for aseptically filling the container.

18. The method according to claim 17 further comprising the step of heating the front and rear sheets in a second localized area to fuse together the heated portions of the adjoining surfaces, thereby forming a peelable seal extending between two sides of the common peripheral edge, the peelable seal separably joining the front and rear sheets to thereby form a first compartment for containing a diluent and a second compartment for containing a medicament.

19. The method according to claim 18, further comprising the step of providing a second sacrificial port interposed between the front and rear sheets, the at least one and second sacrificial ports in communication with the diluent and medicament compartments, respectively.

20. The method according to claim 19 further comprising the steps of:

aseptically filling the diluent compartment with a diluent solution through a respective sacrificial port; and aseptically filling the medicament compartment with a medicament through a respective sacrificial port.

21. The method according to claim 20 further comprising the step of completing the permanent seal along the container's common peripheral edge and removing the sacrificial ports from the container, whereby container formation is completed without being subject to a sterilization step after the compartment filling step.

22. The method according to claim 21, further comprising the step of providing an isolator having a sterile environment, the ambient atmosphere within the isolator maintained in a sterile condition, wherein the diluent compartment and medicament compartment are aseptically filled with pre-sterilized diluent and pre-sterilized medicament in the sterile environment inside the isolator.

23. The method according to claim 21, wherein said peelable seal is formed by maintaining the heat seal temperature in the range of from 245° F. to 265° F. while applying a pressure in the range of from about 230 psi to about 340 psi for a time in the range of from about 1.5 seconds to about 2.5 seconds.

24. The method according to claim 22 further comprising the step of sterilizing said container before the first aseptic compartment filling step.

25. A method for forming a flexible container for combined storage and administration of IV solutions, the method comprising the steps of:

providing a flexible, front sheet;

providing a flexible, vapor impermeable rear sheet, the front and rear sheet sealed together at a common peripheral edge;

heating the front and rear sheets in a first localized area to fuse together the heated portions of the adjoining surfaces, thereby forming a permanent seal, the permanent seal being interrupted along its length to define a channel formed between the front and rear sheets;

providing at least one sacrificial port interposed between the front and rear sheets and in communication with the channel for aseptically filling the container;

aseptically filling the container through the at least one sacrificial port; and completing the seal along the container's common peripheral edge and removing the at least one sacrificial port from the container, whereby container formation is completed without being subject to a sterilization step after the first compartment filling step.

26. The method according to claim 25, wherein the front sheet comprises a polypropylene-polyethylene co-polymer blended with styrene ethylene-butylene styrene elastomer.

27. The method according to claim 26, wherein the polypropylene-polyethylene copolymer is blended with styrene ethylene-butylene styrene elastomer in an about 80%/20% wt/wt ratio.

28. The method according to claim 27, wherein the flexible, vapor impermeable rear sheet comprises a multi-layer laminate formed by the steps of:

providing an inner layer of a polypropylene-polyethylene co-polymer blended with a styrene ethylene-butylene styrene elastomer in an about 80%/20% wt/wt ratio interfacing with the front sheet;

providing an intermediate layer of aluminum foil; and providing an outer thermoplastic layer having a higher melting point than said inner layer.

29. The method according to claim 28, including the steps of:

providing a first peelable seal extending between two opposing sides of the common peripheral edge and separably joining the front and rear sheets to form a compartment containing a diluent;

providing a second peelable seal extending between the two sides of the common peripheral edge and separably joining the front and rear sheets to form thereby an outlet compartment and a compartment containing a medicament which is intermediate the outlet compartment and the diluent compartment;

affixing a clear high-barrier laminate film to the outer surface of the front sheet, the high-barrier laminate film sized to span the front sheet surface between the first and second peelable seals so as to cover the medicament compartment; and separably sealing an opaque high-barrier protective film over the exterior surface of the clear high-barrier laminate film.

30. The method according to claim 29, wherein the opaque, high-barrier protective film comprises an opaque, peelable, multi-layer laminate including:

an inwardly facing layer formed of a modified ethylene vinyl acetate polymer;

an outwardly facing layer formed of a polyester polymer having a higher melting temperature than said modified ethylene vinyl acetate polymer; and an aluminum foil layer intermediate the modified ethylene vinyl acetate layer and the polyester polymer layer.

31. The method according to claim 30, wherein the clear high-barrier laminate film comprises:

a polypropylene inner layer disposed adjacent the outer surface of the container front sheet;

a polyester outer layer; and a clear, transparent high-moisture barrier layer interposed between the inner and outer layers.

32. The method according to claim 31, wherein the clear, high-barrier laminate film further comprises a clear, transparent high-oxygen barrier layer intermediate the polypropylene inner layer and the polyester outer layer.

33. The method according to claim 32, wherein the clear, transparent high-moisture barrier layer is a polymer selected from the group consisting of oriented high-density polyethylene, polychlorotrifluoroethylene, and silica deposited polyethylene terephthalate.

34. The method according to claim 33, wherein the clear, transparent high-oxygen barrier layer is a polymer selected from the group consisting of ethylenevinylalcohol, polyvinylidenechloride coated polyethylene terephthalate, and silica deposited polyvinylalcohol.

35. The method according to claim 30 further comprising the steps of:

folding the container over adjacent the first peelable seal such that the folded-over container's outwardly facing surface comprises the multi-layer laminate rear sheet; and securing the container in a folded-over condition by engaging a locking tab integrally formed with and extending from a side of the container with a slot integrally formed with and extending from the same side of the container as the tab, wherein the tab and slot are moved into position for mutual engagement when the container is folded-over adjacent the first peelable seal to thereby secure the container in a folded over condition.

36. The method according to claim 30, wherein the opaque, high-barrier protective film is separably sealed to the clear high-barrier laminate film by a patterned heat seal head, the pattern forming seal portions alternating with unsealed portions, the sealed portions defining an area smaller than the surface area of the opaque high-barrier film so as to moderate the peel force required to remove the opaque high-barrier film.

37. The method according to claim 29, further including the step of providing a third peelable seal extending between the two sides of the common peripheral edge and separably joining the front and rear sheets to form thereby a sacrificial moisture barrier compartment intermediate the diluent compartment and the medicament compartment.

* * * * *